United States Patent
Sakurai et al.

(10) Patent No.: US 10,155,784 B2
(45) Date of Patent: Dec. 18, 2018

(54) ALCOHOL COMPOUND

(71) Applicant: ADEKA CORPORATION, Tokyo (JP)

(72) Inventors: Atsushi Sakurai, Tokyo (JP); Masako Hatase, Tokyo (JP); Naoki Yamada, Tokyo (JP); Tsubasa Shiratori, Tokyo (JP); Akio Saito, Tokyo (JP); Tomoharu Yoshino, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 15/861,719

(22) Filed: Jan. 4, 2018

(65) Prior Publication Data

US 2018/0134739 A1 May 17, 2018

Related U.S. Application Data

(62) Division of application No. 14/413,102, filed as application No. PCT/JP2013/078493 on Oct. 21, 2013, now Pat. No. 9,896,468.

(30) Foreign Application Priority Data

Nov. 13, 2012 (JP) .................................. 2012-249511

(51) Int. Cl.
*C07C 251/08* (2006.01)
*C07F 15/06* (2006.01)
*C07C 251/04* (2006.01)
*C07F 1/08* (2006.01)
*C07F 15/04* (2006.01)
*C23C 16/18* (2006.01)
*C23C 16/40* (2006.01)
*C07F 7/28* (2006.01)

(52) U.S. Cl.
CPC .......... *C07F 15/065* (2013.01); *C07C 251/04* (2013.01); *C07C 251/08* (2013.01); *C07F 1/08* (2013.01); *C07F 15/045* (2013.01); *C23C 16/18* (2013.01); *C23C 16/406* (2013.01); *C23C 16/408* (2013.01); *C07F 7/28* (2013.01)

(58) Field of Classification Search
None
See application file for complete search history.

(56) References Cited

U.S. PATENT DOCUMENTS

| | | | |
|---|---|---|---|
| 3,872,116 | A | 3/1975 | Gipson |
| 3,954,873 | A | 5/1976 | Gipson |
| 6,369,256 | B1 | 4/2002 | Chi et al. |
| 6,982,341 | B1 | 1/2006 | Kim et al. |
| 2004/0215030 | A1 | 10/2004 | Norman |
| 2005/0033075 | A1 | 2/2005 | Chi |
| 2008/0085365 | A1 | 4/2008 | Yamada et al. |
| 2008/0171890 | A1 | 7/2008 | Kim et al. |
| 2009/0035464 | A1 | 2/2009 | Sato et al. |

FOREIGN PATENT DOCUMENTS

| | | |
|---|---|---|
| JP | 49-61108 | 6/1974 |
| JP | 2003-535839 | 12/2003 |
| JP | 2005-2099 | 1/2005 |
| JP | 2006-143693 | 6/2006 |
| JP | 2006-249046 | 9/2006 |
| JP | 2006-328019 | 12/2006 |
| JP | 2013-032309 | 2/2013 |
| JP | 2013-216614 | 10/2013 |
| KR | 100675983 | 1/2007 |
| WO | 2005085175 | 9/2005 |

OTHER PUBLICATIONS

International Search Report PCT/JP2013/078493 dated Jan. 21, 2014.
Izvestiya Akademii Nauk SSSR, Seriya Khimicheskaya, 1974, vol. 1, p. 206-208, compound (XI).
Ukrainskii Khimicheskii Zhurnal (Russian Edition), 1981, vol. 47, No. 9, p. 959-961, compound (VIIIa).
B.P.Gusev et al.—Reaction of Diacetylenic Glycols With Amines—N.D. Zelinskil Institute of Organic Chemistry, Academy of Science of the USSR, Moscow. Translated from Izvestiya Akademli Nauk SSSR, Seriya Khimicheskaya, No. 1, pp. 196-198, Jan. 1974. Original article submitted Jun. 28, 1973.

*Primary Examiner* — Clinton A Brooks
*Assistant Examiner* — Ana Z Muresan
(74) *Attorney, Agent, or Firm* — Young & Thompson

(57) ABSTRACT

An alcohol compound of formula (II) in which $R^4$ represents a methyl group or an ethyl group, $R^5$ represents a hydrogen atom, and $R^6$ represents a $C_{1-3}$ linear or branched alkyl group. The alcohol compound has physical properties suitable for a material for forming thin films by CVD, and particularly, physical properties suitable for a material for forming metallic-copper thin films.

1 Claim, 8 Drawing Sheets

[Fig.1]
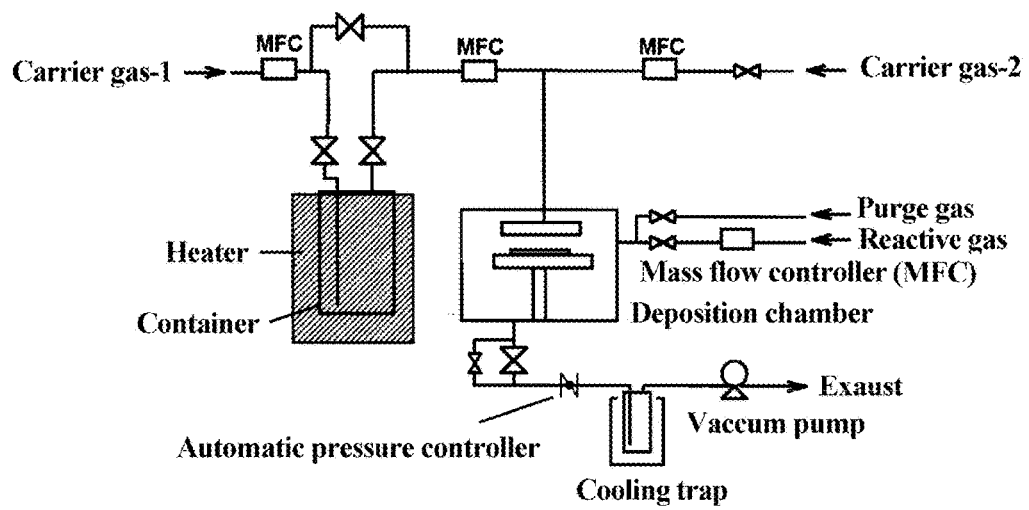
[Fig.2]
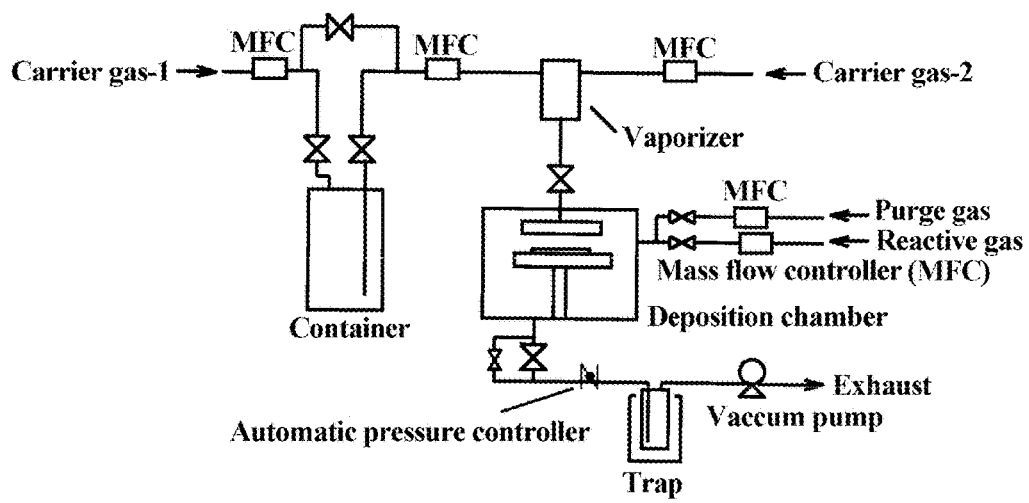

[Fig.3]
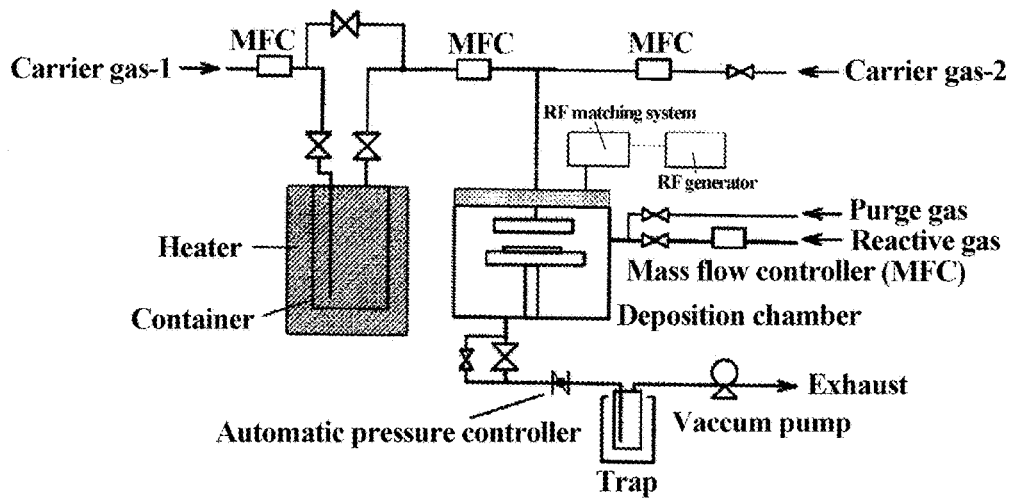
[Fig.4]
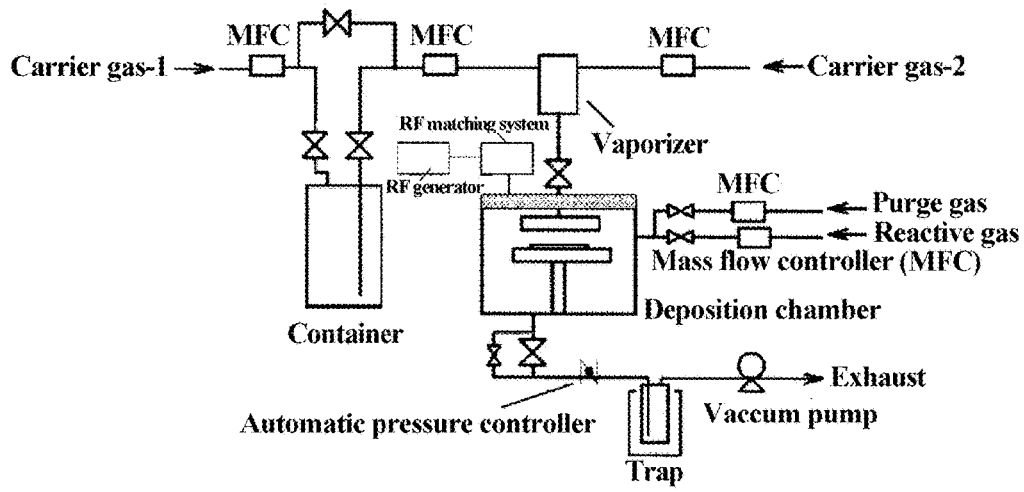

[Fig.5]
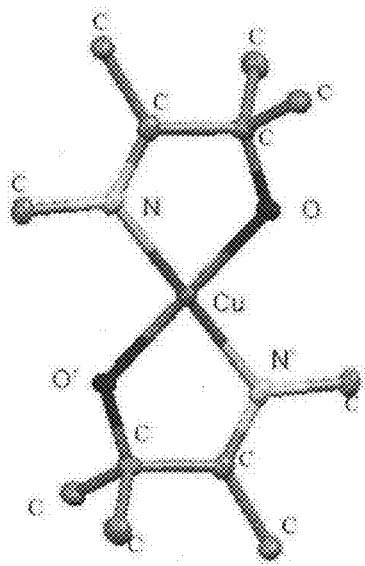
R1;wR2:0.0446;0.1270
[Fig.6]
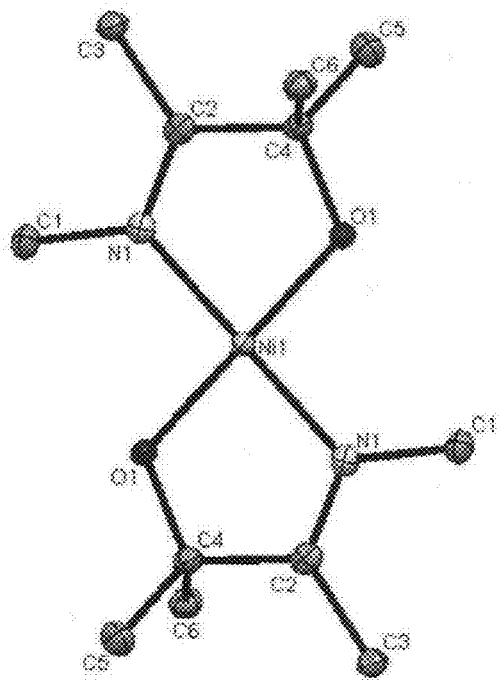
R1;wR2:0.0277;0.0636

[Fig.7]
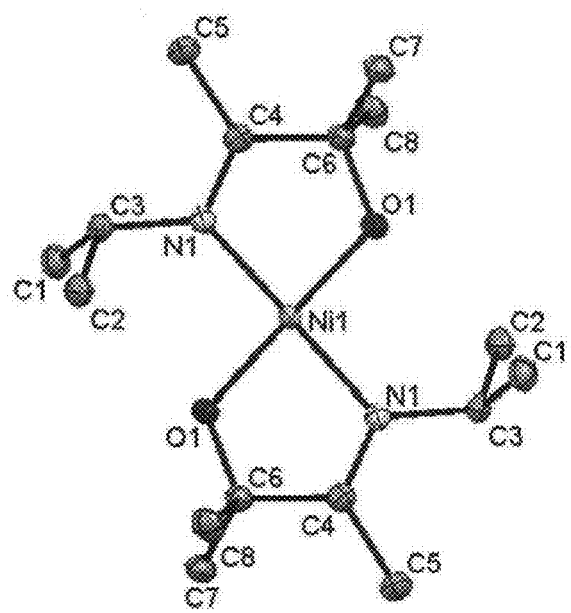
R1;wR2:0.0365;0.0868
[Fig.8]
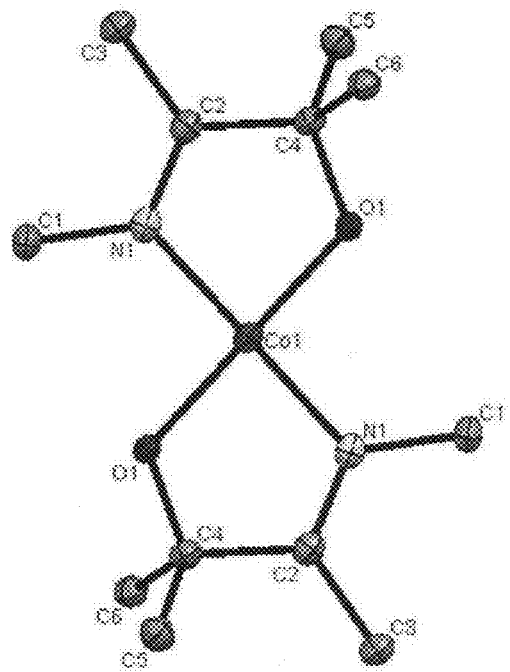
R1;wR2:0.0432;0.1030

[Fig.9]
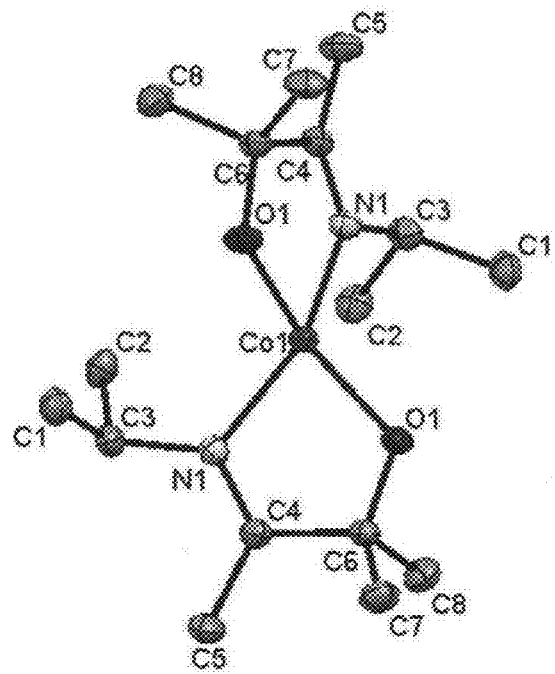
R1;wR2:0.0435;0.1130
[Fig.10]
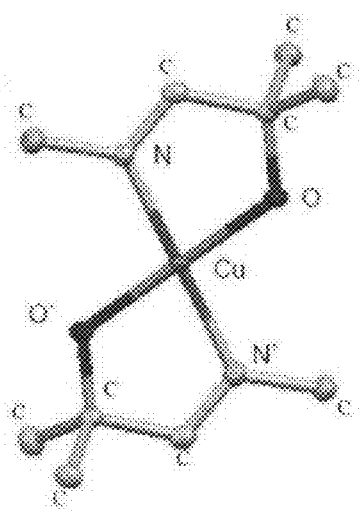
R1;wR2:0.0360;0.0902

[Fig.11]
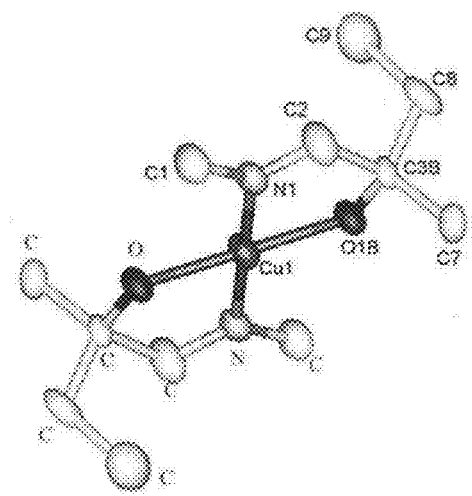
R1;wR2:0.0564;0.1328
[Fig.12]
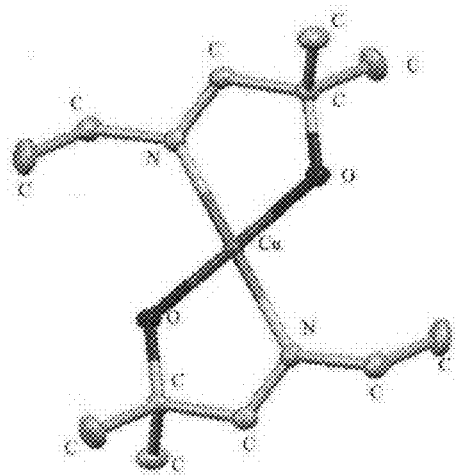
R1;wR2:0.0288;0.0728

[Fig.13]
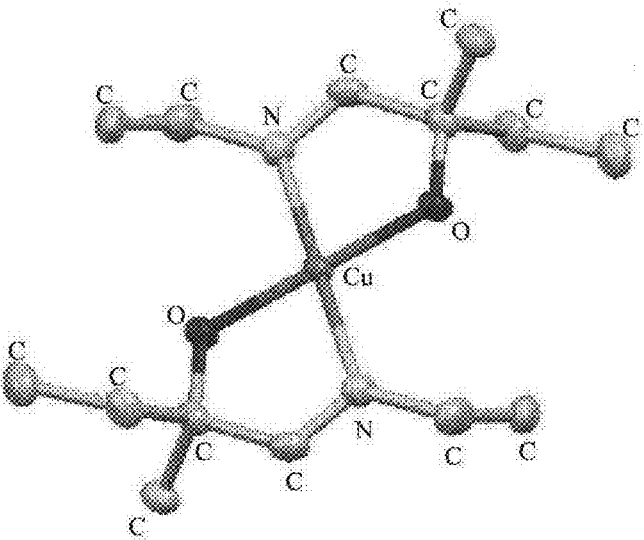
R1;wR2:0.0765;0.1699
[Fig.14]
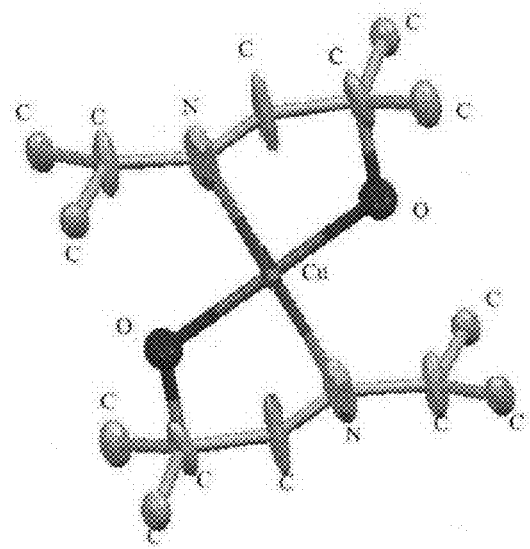
R1;wR2:0.1023;0.2702

[Fig.15]
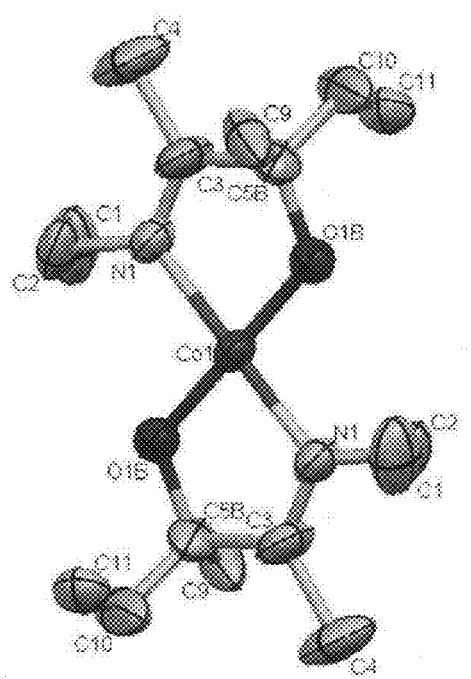

ALCOHOL COMPOUND

TECHNICAL FIELD

The present invention relates to a novel metal alkoxide compound including a specific iminoalcohol as a ligand, a thin-film-forming material including the aforementioned compound, a method for producing a metal-containing thin film by using the aforementioned thin-film-forming material, and a novel alcohol compound.

BACKGROUND ART

Thin-film materials including metal elements exhibit various characteristics, such as electric and optical characteristics, and are thus used for a variety of purposes. For example, copper and copper-containing thin films have the characteristics of high electroconductivity, high electromigration resistance, and high melting point, and are thus used as LSI wiring materials. Nickel and nickel-containing thin films are mainly used for electronic component members such as resistive films and barrier films, recording medium members such as magnetic films, and thin-film solar battery members such as electrodes. Cobalt and cobalt-containing thin films are used for electrode films, resistive films, adhesive films, magnetic tapes, carbide tool members, and the like.

Methods for producing such thin films include sputtering, ion plating, metal organic deposition (MOD) methods such as dipping-pyrolysis methods and sol-gel methods, and chemical vapor deposition. Chemical vapor deposition (also referred to hereinafter simply as CVD), including atomic layer deposition (ALD), is the most suitable production process because of its various advantages, such as that it has excellent composition controllability and ability to cover irregularities, is suitable to mass production, and allows hybrid integration.

Various materials have been reported as metal-supplying sources usable in chemical vapor deposition. For example, Patent Literature 1 discloses a tertiary aminoalkoxide compound of nickel that can be used as a nickel-containing thin-film-forming material for MOCVD. Patent Literature 2 discloses a tertiary aminoalkoxide compound of cobalt that can be used as a cobalt-containing thin-film-forming material for MOCVD. Patent Literature 3 discloses a tertiary aminoalkoxide compound of copper that can be used as a copper-containing thin-film-forming material for chemical vapor deposition.

CITATION LIST

Patent Literature

Patent Literature 1: US 2008/171890 A1
Patent Literature 2: KR 100675983
Patent Literature 3: JP 2006-328019 A

SUMMARY OF INVENTION

Technical Problem

In cases of forming a thin film by vaporizing e.g. a chemical vapor deposition material, a compound (precursor) suitable for such a material needs to have such characteristics as that it does not exhibit spontaneous ignitability, has a high vapor pressure and is easy to vaporize, and has high thermal stability. There has been no conventional metal compound that can sufficiently satisfy these characteristics.

In cases of forming a metallic-copper thin film by vaporizing e.g. a chemical vapor deposition material, there have been such problems as that the quality of the metallic-copper thin film deteriorates when heating is performed at temperatures equal to or above 200° C., the electric resistance value increases, and desired electric characteristics cannot be achieved. The cause of these problems has not yet been identified, but it is thought that these problems are caused by an increase in the particle diameter of copper particles existing in the obtained thin film and/or the agglomeration of such particles due to heating at temperatures equal to or above 200° C. So, there has been a need for a chemical vapor deposition material for forming metallic-copper thin films that undergoes thermal decomposition at temperatures below 200° C.

The present invention provides a metal alkoxide compound having physical properties suitable as a material for forming thin films by CVD, and particularly provides a metal alkoxide compound having physical properties suitable as a material for forming metallic-copper thin films.

Solution to Problem

As a result of elaborate investigation, Inventors have found that specific metal alkoxide compounds can overcome the aforementioned problems, thus arriving at the present invention.

The present invention provides a metal alkoxide compound represented by the following general formula (I), a thin-film-forming material including the same, and a thin film production method for forming a metal-containing thin film by using the aforementioned material.

[Chem. 1]

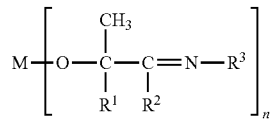

In the formula, $R^1$ represents a methyl group or an ethyl group, $R^2$ represents a hydrogen atom or a methyl group, $R^3$ represents a $C_{1-3}$ linear or branched alkyl group, M represents a metal atom or a silicon atom, and n represents the valence of the metal atom or silicon atom.

The present invention also provides an alcohol compound that is represented by the following general formula (II) and that is suitable as a ligand in the aforementioned metal alkoxide compound.

[Chem. 2]

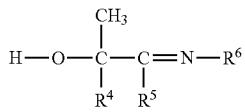

In the formula, $R^4$ represents a methyl group or an ethyl group, $R^5$ represents a hydrogen atom or a methyl group, and $R^6$ represents a $C_{1-3}$ linear or branched alkyl group; if $R^5$ is a hydrogen atom, $R^4$ represents a methyl group or an ethyl group and $R^6$ represents a $C_{1-3}$ linear or branched alkyl group; if $R^5$ is a methyl group and $R^4$ is a methyl group, $R^6$ represents a $C_3$ linear or branched alkyl group; if $R^5$ is a methyl group and $R^4$ is an ethyl group, $R^6$ represents a $C_{1-3}$ linear or branched alkyl group.

Advantageous Effects of Invention

The present invention can provide a novel metal alkoxide compound that does not exhibit spontaneous ignitability, exhibits sufficient volatility, and has high thermal stability. This metal alkoxide compound is suitable as a material for forming thin films by CVD. Further, the present invention can provide a copper compound that does not exhibit spontaneous ignitability, can be thermally decomposed at temperatures below 200° C., and exhibits sufficient volatility. This copper compound is suitable as a thin-film-forming material for forming metallic-copper thin films by CVD. The present invention can also provide a novel alcohol compound suitable as a material for the metal alkoxide compound of the present invention.

BRIEF DESCRIPTION OF DRAWINGS

FIG. 1 is a schematic diagram illustrating an example of a chemical vapor deposition device used for a method for producing a metal-containing thin film according to the present invention.

FIG. 2 is a schematic diagram illustrating another example of a chemical vapor deposition device used for a method for producing a metal-containing thin film according to the present invention.

FIG. 3 is a schematic diagram illustrating another example of a chemical vapor deposition device used for a method for producing a metal-containing thin film according to the present invention.

FIG. 4 is a schematic diagram illustrating another example of a chemical vapor deposition device used for a method for producing a metal-containing thin film according to the present invention.

FIG. 5 is a molecular structure diagram of Compound No. 25 obtained by single-crystal X-ray structural analysis.

FIG. 6 is a molecular structure diagram of Compound No. 41 obtained by single-crystal X-ray structural analysis.

FIG. 7 is a molecular structure diagram of Compound No. 47 obtained by single-crystal X-ray structural analysis.

FIG. 8 is a molecular structure diagram of Compound No. 57 obtained by single-crystal X-ray structural analysis.

FIG. 9 is a molecular structure diagram of Compound No. 63 obtained by single-crystal X-ray structural analysis.

FIG. 10 is a molecular structure diagram of Compound No. 17 obtained by single-crystal X-ray structural analysis.

FIG. 11 is a molecular structure diagram of Compound No. 18 obtained by single-crystal X-ray structural analysis.

FIG. 12 is a molecular structure diagram of Compound No. 19 obtained by single-crystal X-ray structural analysis.

FIG. 13 is a molecular structure diagram of Compound No. 20 obtained by single-crystal X-ray structural analysis.

FIG. 14 is a molecular structure diagram of Compound No. 23 obtained by single-crystal X-ray structural analysis.

FIG. 15 is a molecular structure diagram of Compound No. 60 obtained by single-crystal X-ray structural analysis.

DESCRIPTION OF EMBODIMENTS

A metal alkoxide compound of the present invention is represented by the aforementioned general formula (I), and is suitable as a precursor for a thin-film production method, such as CVD, involving a vaporizing step, and is particularly suitable as a precursor used in ALD because of its high thermal stability.

In the aforementioned general formula (I), $R^1$ represents a methyl group or an ethyl group, $R^2$ represents a hydrogen atom or a methyl group, $R^3$ represents a $C_{1-3}$ linear or branched alkyl group, M represents a metal atom or a silicon atom, and n represents the valence of the metal atom or silicon atom. Examples of the $C_{1-3}$ linear or branched alkyl group represented by $R^3$ include a methyl group, an ethyl group, a propyl group, and an isopropyl group. The metal alkoxide compound represented by the aforementioned general formula (I) may exhibit optical activity; the metal alkoxide compound of the present invention, however, is not particularly differentiated between an R isomer and an S isomer and either is acceptable, and a mixture including R and S isomers at a discretionary ratio is also acceptable. A racemic mixture is inexpensive to produce.

In the aforementioned general formula (I), it is preferable that $R^1$, $R^2$, and $R^3$ give a high vapor pressure and a high thermal decomposition temperature in cases of use in a method for producing a thin film other than metallic copper and involving a step of vaporizing the compound. More specifically, in cases where M is a metal atom other than copper or a silicon atom, $R^1$ is preferably a methyl group or an ethyl group, $R^2$ is preferably a hydrogen atom or a methyl group, and $R^3$ is preferably a methyl group, an ethyl group, or an isopropyl group. In cases where M is copper, $R^1$ is preferably a methyl group or an ethyl group, $R^2$ is preferably a methyl group, and $R^3$ is preferably a methyl group, an ethyl group, or an isopropyl group. In cases of a method for producing a thin film by MOD, which does not involve a vaporizing step, $R^1$, $R^2$, $R^3$ may be selected discretionarily depending on dissolubility to the solvent used, the thin-film formation reaction, and the like.

In the aforementioned general formula (I), it is preferable that $R^1$, $R^2$, and $R^3$ give a high vapor pressure and a thermal decomposition temperature below 200° C. in cases of use in a method for producing a metallic-copper thin film and involving a step of vaporizing the compound. More specifically, M is copper, $R^1$ is preferably a methyl group or an ethyl group, $R^2$ is preferably a hydrogen atom, and $R^3$ is preferably a methyl group, an ethyl group, or an isopropyl group. Among the above, a compound wherein $R^1$ is an ethyl group is particularly preferable because of its low thermal decomposition temperature. In cases of a method for producing a thin film by MOD, which does not involve a vaporizing step, $R^1$, $R^2$, $R^3$ may be selected discretionarily depending on dissolubility to the solvent used, the thin-film formation reaction, and the like.

In the aforementioned general formula (I), M represents a metal atom or a silicon atom. The metal atom is not particularly limited, and examples thereof include lithium, sodium, potassium, magnesium, calcium, strontium, barium, titanium, zirconium, hafnium, vanadium, niobium, tantalum, chromium, molybdenum, tungsten, manganese, iron, ruthenium, cobalt, rhodium, iridium, nickel, palladium, platinum, copper, silver, gold, zinc, aluminum, gallium, indium, germanium, tin, lead, antimony, bismuth, scandium, yttrium, lanthanum, cerium, praseodymium, neodymium, promethium, samarium, europium, gadolinium, terbium, dysprosium, holmium, erbium, thulium, ytterbium, and lutetium.

The metal alkoxide compound of the present invention is typically represented by the aforementioned general formula (I), but is not differentiated from a case where the end donor group in the ligand coordinates with the metal atom and forms a ring structure—i.e., a case where the compound is represented by the following general formula (I-A)—and the present metal alkoxide compound is a concept encompassing both.

[Chem. 3]

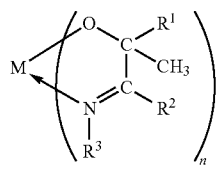
(I-A)

In the formula, $R^1$ represents a methyl group or an ethyl group, $R^2$ represents a hydrogen atom or a methyl group, $R^3$ represents a $C_{1-3}$ linear or branched alkyl group, M represents a metal atom, and n represents the valence of the metal atom.

Concrete examples of metal alkoxide compounds represented by the aforementioned general formula (I) include Compounds Nos. 1 to 16. It should be noted that in Compounds Nos. 1 to 16, M is a metal atom or a silicon atom, and n represents the valence of the metal atom or silicon atom.

[Chem. 4]

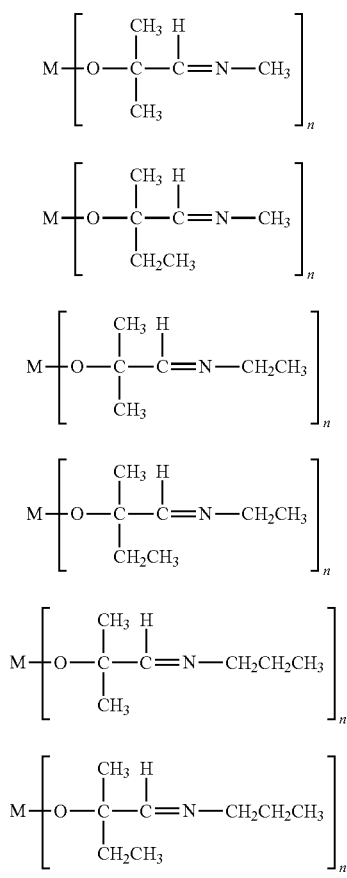

Compound No. 1

Compound No. 2

Compound No. 3

Compound No. 4

Compound No. 5

Compound No. 6

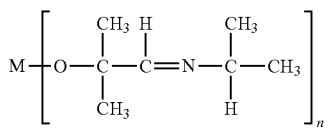
Compound No. 7

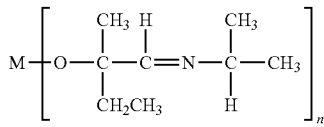
Compound No. 8

[Chem. 5]

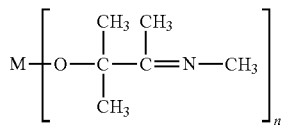
Compound No. 9

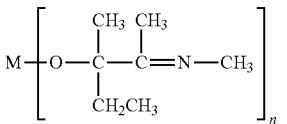
Compound No. 10

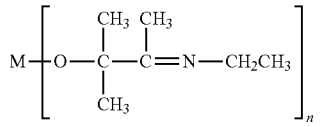
Compound No. 11

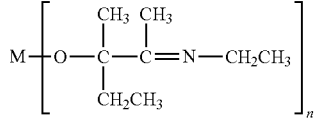
Compound No. 12

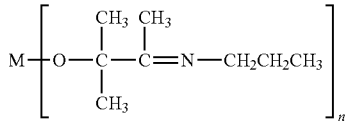
Compound No. 13

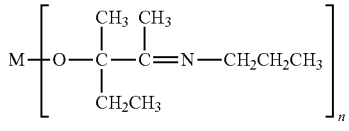
Compound No. 14

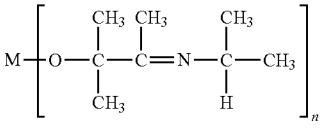
Compound No. 15

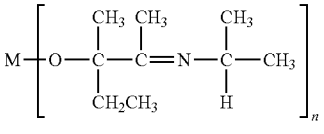
Compound No. 16

Specific examples of compounds represented by the aforementioned general formula (I) include, for example: Compounds Nos. 17 to 32 in cases where M is copper; Compounds Nos. 33 to 48 where M is nickel; and Compounds Nos. 49 to 64 where M is cobalt.

[Chem. 6]

Compound No. 17

$$\text{Cu} + \text{O} - \underset{\underset{\text{CH}_3}{|}}{\overset{\overset{\text{CH}_3}{|}}{\text{C}}} - \underset{}{\overset{\overset{\text{H}}{|}}{\text{C}}} = \text{N} - \text{CH}_3 \Big]_2$$

Compound No. 18

$$\text{Cu} + \text{O} - \underset{\underset{\text{CH}_2\text{CH}_3}{|}}{\overset{\overset{\text{CH}_3}{|}}{\text{C}}} - \underset{}{\overset{\overset{\text{H}}{|}}{\text{C}}} = \text{N} - \text{CH}_3 \Big]_2$$

Compound No. 19

$$\text{Cu} + \text{O} - \underset{\underset{\text{CH}_3}{|}}{\overset{\overset{\text{CH}_3}{|}}{\text{C}}} - \underset{}{\overset{\overset{\text{H}}{|}}{\text{C}}} = \text{N} - \text{CH}_2\text{CH}_3 \Big]_2$$

Compound No. 20

$$\text{Cu} + \text{O} - \underset{\underset{\text{CH}_2\text{CH}_3}{|}}{\overset{\overset{\text{CH}_3}{|}}{\text{C}}} - \underset{}{\overset{\overset{\text{H}}{|}}{\text{C}}} = \text{N} - \text{CH}_2\text{CH}_3 \Big]_2$$

Compound No. 21

$$\text{Cu} + \text{O} - \underset{\underset{\text{CH}_3}{|}}{\overset{\overset{\text{CH}_3}{|}}{\text{C}}} - \underset{}{\overset{\overset{\text{H}}{|}}{\text{C}}} = \text{N} - \text{CH}_2\text{CH}_2\text{CH}_3 \Big]_2$$

Compound No. 22

$$\text{Cu} + \text{O} - \underset{\underset{\text{CH}_2\text{CH}_3}{|}}{\overset{\overset{\text{CH}_3}{|}}{\text{C}}} - \underset{}{\overset{\overset{\text{H}}{|}}{\text{C}}} = \text{N} - \text{CH}_2\text{CH}_2\text{CH}_3 \Big]_2$$

Compound No. 23

$$\text{Cu} + \text{O} - \underset{\underset{\text{CH}_3}{|}}{\overset{\overset{\text{CH}_3}{|}}{\text{C}}} - \underset{}{\overset{\overset{\text{H}}{|}}{\text{C}}} = \text{N} - \underset{\underset{\text{H}}{|}}{\overset{\overset{\text{CH}_3}{|}}{\text{C}}} - \text{CH}_3 \Big]_2$$

Compound No. 24

$$\text{Cu} + \text{O} - \underset{\underset{\text{CH}_2\text{CH}_3}{|}}{\overset{\overset{\text{CH}_3}{|}}{\text{C}}} - \underset{}{\overset{\overset{\text{H}}{|}}{\text{C}}} = \text{N} - \underset{\underset{\text{H}}{|}}{\overset{\overset{\text{CH}_3}{|}}{\text{C}}} - \text{CH}_3 \Big]_2$$

[Chem. 7]

Compound No. 25

$$\text{Cu} + \text{O} - \underset{\underset{\text{CH}_3}{|}}{\overset{\overset{\text{CH}_3}{|}}{\text{C}}} - \underset{}{\overset{\overset{\text{CH}_3}{|}}{\text{C}}} = \text{N} - \text{CH}_3 \Big]_2$$

Compound No. 26

$$\text{Cu} + \text{O} - \underset{\underset{\text{CH}_2\text{CH}_3}{|}}{\overset{\overset{\text{CH}_3}{|}}{\text{C}}} - \underset{}{\overset{\overset{\text{CH}_3}{|}}{\text{C}}} = \text{N} - \text{CH}_3 \Big]_2$$

Compound No. 27

$$\text{Cu} + \text{O} - \underset{\underset{\text{CH}_3}{|}}{\overset{\overset{\text{CH}_3}{|}}{\text{C}}} - \underset{}{\overset{\overset{\text{CH}_3}{|}}{\text{C}}} = \text{N} - \text{CH}_2\text{CH}_3 \Big]_2$$

Compound No. 28

$$\text{Cu} + \text{O} - \underset{\underset{\text{CH}_2\text{CH}_3}{|}}{\overset{\overset{\text{CH}_3}{|}}{\text{C}}} - \underset{}{\overset{\overset{\text{CH}_3}{|}}{\text{C}}} = \text{N} - \text{CH}_2\text{CH}_3 \Big]_2$$

Compound No. 29

$$\text{Cu} + \text{O} - \underset{\underset{\text{CH}_3}{|}}{\overset{\overset{\text{CH}_3}{|}}{\text{C}}} - \underset{}{\overset{\overset{\text{CH}_3}{|}}{\text{C}}} = \text{N} - \text{CH}_2\text{CH}_3 \Big]_2$$

Compound No. 30

$$\text{Cu} + \text{O} - \underset{\underset{\text{CH}_2\text{CH}_3}{|}}{\overset{\overset{\text{CH}_3}{|}}{\text{C}}} - \underset{}{\overset{\overset{\text{CH}_3}{|}}{\text{C}}} = \text{N} - \text{CH}_2\text{CH}_3 \Big]_2$$

Compound No. 31

$$\text{Cu} + \text{O} - \underset{\underset{\text{CH}_3}{|}}{\overset{\overset{\text{CH}_3}{|}}{\text{C}}} - \underset{}{\overset{\overset{\text{CH}_3}{|}}{\text{C}}} = \text{N} - \underset{\underset{\text{H}}{|}}{\overset{\overset{\text{CH}_3}{|}}{\text{C}}} - \text{CH}_3 \Big]_2$$

Compound No. 32

$$\text{Cu} + \text{O} - \underset{\underset{\text{CH}_2\text{CH}_3}{|}}{\overset{\overset{\text{CH}_3}{|}}{\text{C}}} - \underset{}{\overset{\overset{\text{CH}_3}{|}}{\text{C}}} = \text{N} - \underset{\underset{\text{H}}{|}}{\overset{\overset{\text{CH}_3}{|}}{\text{C}}} - \text{CH}_3 \Big]_2$$

[Chem. 8]

Compound No. 33

$$\text{Ni} + \text{O} - \underset{\underset{\text{CH}_3}{|}}{\overset{\overset{\text{CH}_3}{|}}{\text{C}}} - \underset{}{\overset{\overset{\text{H}}{|}}{\text{C}}} = \text{N} - \text{CH}_3 \Big]_2$$

Compound No. 34

$$\text{Ni} + \text{O} - \underset{\underset{\text{CH}_2\text{CH}_3}{|}}{\overset{\overset{\text{CH}_3}{|}}{\text{C}}} - \underset{}{\overset{\overset{\text{H}}{|}}{\text{C}}} = \text{N} - \text{CH}_3 \Big]_2$$

Compound No. 35

$$\text{Ni} + \text{O} - \underset{\underset{\text{CH}_3}{|}}{\overset{\overset{\text{CH}_3}{|}}{\text{C}}} - \underset{}{\overset{\overset{\text{H}}{|}}{\text{C}}} = \text{N} - \text{CH}_2\text{CH}_3 \Big]_2$$

Compound No. 36

$$\text{Ni} + \text{O} - \underset{\underset{\text{CH}_2\text{CH}_3}{|}}{\overset{\overset{\text{CH}_3}{|}}{\text{C}}} - \underset{}{\overset{\overset{\text{H}}{|}}{\text{C}}} = \text{N} - \text{CH}_2\text{CH}_3 \Big]_2$$

Compound No. 37

$$\text{Ni} + \text{O} - \underset{\underset{\text{CH}_3}{|}}{\overset{\overset{\text{CH}_3}{|}}{\text{C}}} - \underset{}{\overset{\overset{\text{H}}{|}}{\text{C}}} = \text{N} - \text{CH}_2\text{CH}_2\text{CH}_3 \Big]_2$$

Compound No. 38

$$\text{Ni} + \text{O} - \underset{\underset{\text{CH}_2\text{CH}_3}{|}}{\overset{\overset{\text{CH}_3}{|}}{\text{C}}} - \underset{}{\overset{\overset{\text{H}}{|}}{\text{C}}} = \text{N} - \text{CH}_2\text{CH}_2\text{CH}_3 \Big]_2$$

-continued

Compound No. 39

Ni$-\left[ O-\underset{\underset{CH_3}{|}}{\overset{\overset{CH_3}{|}}{C}}-\underset{\underset{H}{|}}{\overset{\overset{H}{|}}{C}}=N-\underset{\underset{H}{|}}{\overset{\overset{CH_3}{|}}{C}}-CH_3 \right]_2$ Compound No. 40

Ni$-\left[ O-\underset{\underset{CH_2CH_3}{|}}{\overset{\overset{CH_3}{|}}{C}}-\underset{\underset{H}{|}}{\overset{\overset{H}{|}}{C}}=N-\underset{\underset{H}{|}}{\overset{\overset{CH_3}{|}}{C}}-CH_3 \right]_2$

[Chem. 9]

Compound No. 41

Ni$-\left[ O-\underset{\underset{CH_3}{|}}{\overset{\overset{CH_3}{|}}{C}}-\overset{\overset{CH_3}{|}}{C}=N-CH_3 \right]_2$ Compound No. 42

Ni$-\left[ O-\underset{\underset{CH_2CH_3}{|}}{\overset{\overset{CH_3}{|}}{C}}-\overset{\overset{CH_3}{|}}{C}=N-CH_3 \right]_2$ Compound No. 43

Ni$-\left[ O-\underset{\underset{CH_3}{|}}{\overset{\overset{CH_3}{|}}{C}}-\overset{\overset{CH_3}{|}}{C}=N-CH_2CH_3 \right]_2$ Compound No. 44

Ni$-\left[ O-\underset{\underset{CH_2CH_3}{|}}{\overset{\overset{CH_3}{|}}{C}}-\overset{\overset{CH_3}{|}}{C}=N-CH_2CH_3 \right]_2$ Compound No. 45

Ni$-\left[ O-\underset{\underset{CH_3}{|}}{\overset{\overset{CH_3}{|}}{C}}-\overset{\overset{CH_3}{|}}{C}=N-CH_2CH_2CH_3 \right]_2$ Compound No. 46

Ni$-\left[ O-\underset{\underset{CH_2CH_3}{|}}{\overset{\overset{CH_3}{|}}{C}}-\overset{\overset{CH_3}{|}}{C}=N-CH_2CH_2CH_3 \right]_2$ Compound No. 47

Ni$-\left[ O-\underset{\underset{CH_3}{|}}{\overset{\overset{CH_3}{|}}{C}}-\overset{\overset{CH_3}{|}}{C}=N-\underset{\underset{H}{|}}{\overset{\overset{CH_3}{|}}{C}}-CH_3 \right]_2$ Compound No. 48

Ni$-\left[ O-\underset{\underset{CH_2CH_3}{|}}{\overset{\overset{CH_3}{|}}{C}}-\overset{\overset{CH_3}{|}}{C}=N-\underset{\underset{H}{|}}{\overset{\overset{CH_3}{|}}{C}}-CH_3 \right]_2$

[Chem. 10]

Compound No. 49

Co$-\left[ O-\underset{\underset{CH_3}{|}}{\overset{\overset{CH_3}{|}}{C}}-\underset{\underset{}{}}{\overset{\overset{H}{|}}{C}}=N-CH_3 \right]_2$ Compound No. 50

Co$-\left[ O-\underset{\underset{CH_2CH_3}{|}}{\overset{\overset{CH_3}{|}}{C}}-\overset{\overset{H}{|}}{C}=N-CH_3 \right]_2$ Compound No. 51

Co$-\left[ O-\underset{\underset{CH_3}{|}}{\overset{\overset{CH_3}{|}}{C}}-\overset{\overset{H}{|}}{C}=N-CH_2CH_3 \right]_2$ Compound No. 52

Co$-\left[ O-\underset{\underset{CH_2CH_3}{|}}{\overset{\overset{CH_3}{|}}{C}}-\overset{\overset{H}{|}}{C}=N-CH_2CH_3 \right]_2$ Compound No. 53

Co$-\left[ O-\underset{\underset{CH_3}{|}}{\overset{\overset{CH_3}{|}}{C}}-\overset{\overset{H}{|}}{C}=N-CH_2CH_2CH_3 \right]_2$ Compound No. 54

Co$-\left[ O-\underset{\underset{CH_2CH_3}{|}}{\overset{\overset{CH_3}{|}}{C}}-\overset{\overset{H}{|}}{C}=N-CH_2CH_2CH_3 \right]_2$ Compound No. 55

Co$-\left[ O-\underset{\underset{CH_3}{|}}{\overset{\overset{CH_3}{|}}{C}}-\overset{\overset{H}{|}}{C}=N-\underset{\underset{H}{|}}{\overset{\overset{CH_3}{|}}{C}}-CH_3 \right]_2$ Compound No. 56

Co$-\left[ O-\underset{\underset{CH_2CH_3}{|}}{\overset{\overset{CH_3}{|}}{C}}-\overset{\overset{H}{|}}{C}=N-\underset{\underset{H}{|}}{\overset{\overset{CH_3}{|}}{C}}-CH_3 \right]_2$

[Chem. 11]

Compound No. 57

Co$-\left[ O-\underset{\underset{CH_3}{|}}{\overset{\overset{CH_3}{|}}{C}}-\overset{\overset{CH_3}{|}}{C}=N-CH_3 \right]_2$ Compound No. 58

Co$-\left[ O-\underset{\underset{CH_2CH_3}{|}}{\overset{\overset{CH_3}{|}}{C}}-\overset{\overset{CH_3}{|}}{C}=N-CH_3 \right]_2$ Compound No. 59

Co$-\left[ O-\underset{\underset{CH_3}{|}}{\overset{\overset{CH_3}{|}}{C}}-\overset{\overset{CH_3}{|}}{C}=N-CH_2CH_3 \right]_2$ Compound No. 60

Co$-\left[ O-\underset{\underset{CH_2CH_3}{|}}{\overset{\overset{CH_3}{|}}{C}}-\overset{\overset{CH_3}{|}}{C}=N-CH_2CH_3 \right]_2$

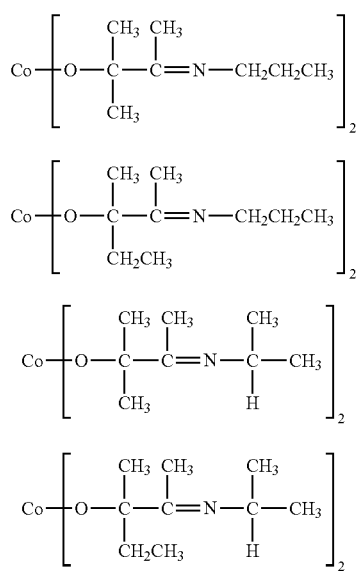

Compound No. 61

Compound No. 62

Compound No. 63

Compound No. 64

The metal alkoxide compound of the present invention is not particularly limited by the production method thereof, and is produced by applying known reactions. As an example of the production method, the present compound can be obtained by reacting an alkoxide compound, a chloride, an amine compound, or the like, of a metal with an alcohol compound having a corresponding structure.

The thin-film-forming material of the present invention is a material employing the above-described metal alkoxide compound of the present invention as a precursor for a thin film, and the form of the thin-film-forming material differs depending on the production process to which it is applied. For example, in cases of producing a thin film including only one type of metal or silicon, the thin-film-forming material of the present invention includes no metal compound or semimetal compound other than the aforementioned metal alkoxide compound. On the other hand, in cases of producing a thin film including two or more types of metals and/or semimetals, the thin-film-forming material of the present invention includes a compound including the desired metal(s) and/or a compound including the desired semimetal(s) (referred to hereinafter also as "other precursor") in addition to the aforementioned metal alkoxide compound.

As described further below, the thin-film-forming material of the present invention may further include an organic solvent and/or a nucleophilic reagent. As described above, in the thin-film-forming material of the present invention, the physical properties of the metal alkoxide compound, which is the precursor, are suitable for CVD and ALD, and thus, the thin-film-forming material is particularly useful as a chemical vapor deposition material (referred to hereinafter also as "CVD material").

In cases where the thin-film-forming material of the present invention is a chemical vapor deposition material, the form thereof is chosen as appropriate depending on, for example, the transporting/supplying method employed in CVD.

Examples of the aforementioned transporting/supplying method include: a gas transportation method in which a CVD material is heated and/or depressurized in a container for storing the material (also referred to hereinafter simply as "material container") and vaporized into vapor, and the vapor is introduced, along with a carrier gas—such as argon, nitrogen, or helium—used as necessary, into a deposition chamber (referred to hereinafter also as "deposition reaction unit") in which a substrate is placed; and a liquid transportation method in which a CVD material is transported to a vaporizing chamber in a liquid or solution state, the material is heated and/or depressurized in the vaporizing chamber and vaporized into vapor, and the vapor is introduced into a deposition chamber. In cases of employing the gas transportation method, the metal alkoxide compound itself represented by the general formula (I) can be used as the CVD material. In cases of employing the liquid transportation method, the metal alkoxide compound itself represented by the general formula (I), or a solution obtained by dissolving the compound in an organic solvent, can be used as the CVD material. The CVD material may further include other precursors, a nucleophilic reagent, or the like.

Further, multi-component CVD methods include: a method in which each of the components of the CVD material is vaporized and supplied independently (referred to hereinafter also as "single-source method"); and a method in which a mixed material including multi-component materials that have been mixed in advance at a desired composition is vaporized and supplied (referred to hereinafter also as "cocktail-source method"). In cases of the cocktail-source method, a mixture of the metal alkoxide compound of the present invention and another precursor, or a mixed solution in which this mixture is dissolved in an organic solvent, may be used as the CVD material. This mixture or mixed solution may further include a nucleophilic reagent or the like. It should be noted that, in cases of using only the metal alkoxide compound of the present invention as the precursor and employing both R and S isomers, a CVD material including the R isomer and a CVD material including the S isomer may be vaporized separately, or a CVD material including a mixture of the R and S isomers may be vaporized.

As for the aforementioned organic solvent, any generally known organic solvent may be used without particularly limitation. Examples of the organic solvent include: acetic esters, such as ethyl acetate, butyl acetate, and methoxyethyl acetate; ethers, such as tetrahydrofuran, tetrahydropyran, ethylene glycol dimethyl ether, diethylene glycol dimethyl ether, triethylene glycol dimethyl ether, dibutyl ether, and dioxane; ketones, such as methylbutyl ketone, methylisobutyl ketone, ethylbutyl ketone, dipropyl ketone, diisobutyl ketone, methylamyl ketone, cyclohexanone, and methylcyclohexanone; hydrocarbons, such as hexane, cyclohexane, methylcyclohexane, dimethylcyclohexane, ethylcyclohexane, heptane, octane, toluene, and xylene; cyano-group-containing hydrocarbons, such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene; pyridine; and lutidine. Depending on, for example, the dissolubility of the solute and/or the relationship between the usage temperature and the boiling point/flash point, the solvent may be used singly, or a mixed solvent including two or more types of solvents may be used. In cases of using the aforementioned organic solvent(s), it is preferable that the total amount of precursor(s) in the CVD material, which is a solution in which the precursor(s) has/have been dissolved in the organic solvent(s), is 0.01 to 2.0 mol/L, and more preferably 0.05 to 1.0 mol/L. The "total amount of precursor(s)" refers to: the amount of the metal alkoxide compound of the present invention in cases where the thin-film-forming material of the present invention does not include any metal compound or semimetal compound other than the metal alkoxide compound of the present invention; and the total amount of the metal alkoxide compound of the present invention and other precursor(s) in cases where the thin-film-forming material of the present invention includes other metal-containing compound(s) and/or semimetal-containing compound(s) in addition to the present metal alkoxide compound.

In cases of employing multi-component CVD, any generally known precursor used as a CVD material may be used without particularly limitation as the other precursor(s) used with the metal alkoxide compound of the present invention.

Examples of other precursors include compounds formed between silicon or a metal and one or more types of compounds selected from a group of compounds usable as organic ligands, such as alcohol compounds, glycol compounds, β-diketone compounds, cyclopentadiene compounds, and organic amine compounds. Examples of metal species in the precursors include lithium, sodium, potassium, magnesium, calcium, strontium, barium, titanium, zirconium, hafnium, vanadium, niobium, tantalum, chromium, molybdenum, tungsten, manganese, iron, ruthenium, cobalt, rhodium, iridium, nickel, palladium, platinum, copper, silver, gold, zinc, aluminum, gallium, indium, germanium, tin, lead, antimony, bismuth, scandium, yttrium, lanthanum, cerium, praseodymium, neodymium, promethium, samarium, europium, gadolinium, terbium, dysprosium, holmium, erbium, thulium, ytterbium, and lutetium.

Examples of alcohol compounds usable as organic ligands in the aforementioned other precursors include: alkyl alcohols, such as methanol, ethanol, propanol, isopropyl alcohol, butanol, secondary butyl alcohol, isobutyl alcohol, tertiary butyl alcohol, pentyl alcohol, isopentyl alcohol, and tertiary pentyl alcohol; ether alcohols, such as 2-methoxyethanol, 2-ethoxyethanol, 2-butoxyethanol, 2-(2-methoxyethoxy)ethanol, 2-methoxy-1-methylethanol, 2-methoxy-1,1-dimethylethanol, 2-ethoxy-1,1-dimethylethanol, 2-isopropoxy-1,1-dimethylethanol, 2-butoxy-1,1-dimethylethanol, 2-(2-methoxyethoxy)-1,1-dimethylethanol, 2-propoxy-1,1-diethylethanol, 2-s-butoxy-1,1-diethylethanol, and 3-methoxy-1,1-dimethylpropanol; and dialkylaminoalcohols, such as dimethylaminoethanol, ethylmethylaminoethanol, diethylaminoethanol, dimethylamino-2-pentanol, ethylmethylamino-2-pentanol, dimethylamino-2-methyl-2-pentanol, ethylmethylamino-2-methyl-2-pentanol, and diethylamino-2-methyl-2-pentanol.

Examples of glycol compounds usable as organic ligands in the aforementioned other precursors include 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3-propanediol, 2-methyl-2,4-pentanediol, 2,4-hexanediol, and 2,4-dimethyl-2,4-pentanediol.

Examples of β-diketone compounds include: alkyl-substituted β-diketones, such as acetylacetone, hexane-2,4-dione, 5-methylhexane-2,4-dione, heptane-2,4-dione, 2-methylheptane-3,5-dione, 5-methylheptane-2,4-dione, 6-methylheptane-2,4-dione, 2,2-dimethylheptane-3,5-dione, 2,6-dimethylheptane-3,5-dione, 2,2,6-trimethylheptane-3,5-dione, 2,2,6,6-tetramethylheptane-3,5-dione, octane-2,4-dione, 2,2,6-trimethyloctane-3,5-dione, 2,6-dimethyloctane-3,5-dione, 2,9-dimethylnonane-4,6-dione, 2-methyl-6-ethyldecane-3,5-dione, and 2,2-dimethyl-6-ethyldecane-3,5-dione; fluorine-substituted alkyl β-diketones, such as 1,1,1-trifluoropentane-2,4-dione, 1,1,1-trifluoro-5,5-dimethylhexane-2,4-dione, 1,1,1,5,5,5-hexafluoropentane-2,4-dione, and 1,3-diperfluorohexylpropane-1,3-dione; and ether-substituted β-diketones, such as 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxy)heptane-3,5-dione.

Examples of cyclopentadiene compounds include cyclopentadiene, methylcyclopentadiene, ethylcyclopentadiene, propylcyclopentadiene, isopropylcyclopentadiene, butylcyclopentadiene, secondary butylcyclopentadiene, isobutylcyclopentadiene, tertiary butylcyclopentadiene, dimethylcyclopentadiene, and tetramethylcyclopentadiene. Examples of organic amine compounds usable as the aforementioned organic ligands include methylamine, ethylamine, propylamine, isopropylamine, butylamine, secondary butylamine, tertiary butylamine, isobutylamine, dimethylamine, diethylamine, dipropylamine, diisopropylamine, ethylmethylamine, propylmethylamine, and isopropylmethylamine.

The aforementioned other precursors are known in this technical field, and methods for producing the same are also known. An example of a method for producing a precursor is as follows. For example, in cases of using an alcohol compound as an organic ligand, a precursor can be produced by reacting an inorganic salt of the aforementioned metal or a hydrate thereof with an alkali metal alkoxide of the alcohol compound. Examples of an inorganic salt of metal or a hydrate thereof may include a halide or a nitrate of the metal. Examples of an alkali metal alkoxide may include sodium alkoxide, lithium alkoxide, and potassium alkoxide.

In cases of employing the single-source method, the other precursor is preferably a compound that has a thermal and/or oxidative decomposition behavior similar to that of the metal alkoxide compound of the present invention. In cases of employing the cocktail-source method, the other precursor is preferably a compound that does not undergo alteration due to chemical reaction etc. at the time of mixing, in addition to having a thermal and/or oxidative decomposition behavior similar to that of the present metal alkoxide compound.

Of the aforementioned other precursors, examples of precursors including titanium, zirconium, or hafnium include compounds represented by the following general formulas (II-1) to (II-5).

[Chem. 12]

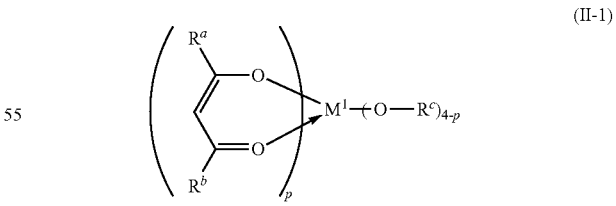

(II-1)

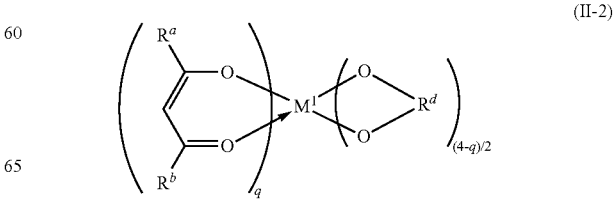

(II-2)

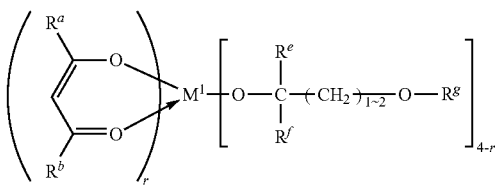

(II-3)

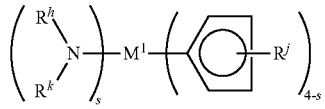

(II-4)

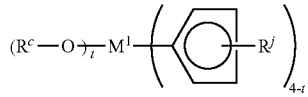

(II-5)

In the formula, $M^1$ represents titanium, zirconium, or hafnium, $R^a$ and $R^b$ each independently represent a $C_{1-20}$ alkyl group that may be substituted by a halogen atom and that may include an oxygen atom in its chain, $R^c$ represents a $C_{1-8}$ alkyl group, $R^d$ represents a $C_{2-18}$ alkylene group that may be branched, $R^e$ and $R^f$ each independently represent a hydrogen atom or a $C_{1-3}$ alkyl group, $R^g$, $R^h$, $R^k$, and $R^j$ each independently represent a hydrogen atom or a $C_{1-4}$ alkyl group, p represents an integer of 0 to 4, q represents 0 or 2, r represents an integer of 0 to 3, s represents an integer of 0 to 4, and t represents an integer of 1 to 4.)

In the formulas (II-1) to (II-5), examples of the $C_{1-20}$ alkyl group that may be substituted by a halogen atom and that may include an oxygen atom in its chain, as represented by $R^a$ and $R^b$, include methyl, ethyl, propyl, isopropyl, butyl, secondary butyl, tertiary butyl, isobutyl, amyl, isoamyl, secondary amyl, tertiary amyl, hexyl, cyclohexyl, 1-methylcyclohexyl, heptyl, 3-heptyl, isoheptyl, tertiary heptyl, n-octyl, isooctyl, tertiary octyl, 2-ethylhexyl, trifluoromethyl, perfluorohexyl, 2-methoxyethyl, 2-ethoxyethyl, 2-butoxyethyl, 2-(2-methoxyethoxy)ethyl, 1-methoxy-1,1-dimethylmethyl, 2-methoxy-1,1-dimethylethyl, 2-ethoxy-1,1-dimethylethyl, 2-isopropoxy-1,1-dimethylethyl, 2-butoxy-1,1-dimethylethyl, and 2-(2-methoxyethoxy)-1,1-dimethylethyl. Examples of the $C_{1-8}$ alkyl group represented by $R^c$ include methyl, ethyl, propyl, isopropyl, butyl, secondary butyl, tertiary butyl, isobutyl, amyl, isoamyl, secondary amyl, tertiary amyl, hexyl, 1-ethylpentyl, cyclohexyl, 1-methylcyclohexyl, heptyl, isoheptyl, tertiary heptyl, n-octyl, isooctyl, tertiary octyl, and 2-ethylhexyl. The $C_{2-18}$ alkylene group that may be branched, as represented by $R^d$, is a group resulting from a glycol, and examples of such a glycol include 1,2-ethanediol, 1,2-propanediol, 1,3-propanediol, 1,3-butanediol, 2,4-hexanediol, 2,2-dimethyl-1,3-propanediol, 2,2-diethyl-1,3-propanediol, 2,2-diethyl-1,3-butanediol, 2-ethyl-2-butyl-1,3-propanediol, 2,4-pentanediol, 2-methyl-1,3-propanediol, and 1-methyl-2,4-pentanediol. Examples of the $C_{1-3}$ alkyl group represented by $R^e$ and $R^f$ include methyl, ethyl, propyl, and 2-propyl. Examples of the $C_{1-4}$ alkyl group represented by $R^g$, $R^h$, $R^j$, and $R^k$ include methyl, ethyl, propyl, isopropyl, butyl, secondary butyl, tertiary butyl, and isobutyl.

Concrete examples of titanium-containing precursors include: tetrakis-alkoxy titanium, such as tetrakis(ethoxy) titanium, tetrakis(2-propoxy)titanium, tetrakis(butoxy)titanium, tetrakis(secondary butoxy)titanium, tetrakis(isobutoxy)titanium, tetrakis(tertiary butoxy)titanium, tetrakis (tertiary amyl)titanium, and tetrakis(1-methoxy-2-methyl-2-propoxy)titanium; tetrakis β-diketonato titanium, such as tetrakis(pentane-2,4-dionato)titanium, (2,6-dimethylheptane-3,5-dionato)titanium, and tetrakis(2,2,6,6-tetramethylheptane-3,5-dionato)titanium; bis(alkoxy)bis(β-diketonato) titanium, such as bis(methoxy)bis(pentane-2,4-dionato) titanium, bis(ethoxy)bis(pentane-2,4-dionato)titanium, bis (tertiary butoxy)bis(pentane-2,4-dionato)titanium, bis (methoxy)bis(2,6-dimethylheptane-3,5-dionato)titanium, bis(ethoxy)bis(2,6-dimethylheptane-3,5-dionato)titanium, bis(2-propoxy)bis(2,6-dimethylheptane-3,5-dionato)titanium, bis(tertiary butoxy)bis(2,6-dimethylheptane-3,5-dionato)titanium, bis(tertiary amyloxy)bis(2,6-dimethylheptane-3,5-dionato)titanium, bis(methoxy)bis(2,2,6,6-tetramethylheptane-3,5-dionato)titanium, bis(ethoxy)bis(2,2,6,6-tetramethylheptane-3,5-dionato)titanium, bis(2-propoxy)bis(2,6,6,6-tetramethylheptane-3,5-dionato) titanium, bis(tertiary butoxy)bis(2,2,6,6-tetramethylheptane-3,5-dionato)titanium, and bis(tertiary amyloxy)bis(2,2,6,6-tetramethylheptane-3,5-dionato)titanium; glycoxy bis(β-diketonato)titanium, such as (2-methylpentane dioxy)bis(2,2,6,6-tetramethylheptane-3,5-dionato)titanium, and (2-methylpentane dioxy)bis(2,6-dimethylheptane-3,5-dionato)titanium; (cyclopentadienyl) tris(dialkylamino)titanium, such as (methylcyclopentadienyl)tris(dimethylamino)titanium, (ethylcyclopentadienyl)tris(dimethylamino)titanium, (cyclopentadienyl)tris(dimethylamino)titanium, (methylcyclopentadienyl)tris(ethylmethylamino)titanium, (ethylcyclopentadienyl)tris(ethylmethylamino)titanium, (cyclopentadienyl)tris(ethylmethylamino)titanium, (methylcyclopentadienyl)tris(diethylamino)titanium, (ethylcyclopentadienyl)tris(diethylamino)titanium, and (cyclopentadienyl)tris(diethylamino)titanium; and (cyclopentadienyl)tris (alkoxy)titanium, such as (cyclopentadienyl)tris(methoxy) titanium, (methylcyclopentadienyl)tris(methoxy)titanium, (ethylcyclopentadienyl)tris(methoxy)titanium, (propylcyclopentadienyl)tris(methoxy)titanium, (isopropylcyclopentadienyl)tris(methoxy)titanium, (butylcyclopentadienyl)tris (methoxy)titanium, (isobutylcyclopentadienyl)tris (methoxy)titanium, and (tertiary butylcyclopentadienyl)tris (methoxy)titanium. Examples of zirconium-containing precursors or hafnium-containing precursors include compounds in which the titanium in the aforementioned compounds given as examples of the titanium-containing precursors is substituted by zirconium or hafnium.

Examples of precursors containing a rare-earth element include compounds represented by the following formulas (III-1) to (III-3).

[Chem. 13]

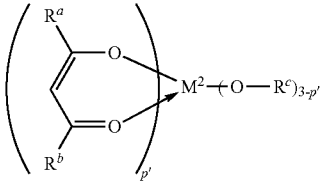

(III-1)

(III-2)

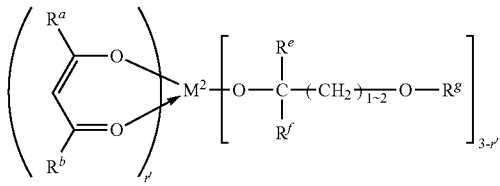

(III-3)

In the formula, $M^2$ represents a rare-earth atom, $R^a$ and $R^b$ each independently represent a $C_{1-20}$ alkyl group that may be substituted by a halogen atom and that may include an oxygen atom in its chain, $R^c$ represents a $C_{1-8}$ alkyl group, $R^e$ and $R^f$ each independently represent a hydrogen atom or a $C_{1-3}$ alkyl group, $R^g$ and $R^j$ each independently represent a $C_{1-4}$ alkyl group, p' represents an integer of 0 to 3, and r' represents an integer of 0 to 2.

In the aforementioned precursor containing a rare-earth element, examples of the rare-earth atom represented by $M^2$ include scandium, yttrium, lanthanum, cerium, praseodymium, neodymium, promethium, samarium, europium, gadolinium, terbium, dysprosium, holmium, erbium, thulium, ytterbium, and lutetium, and examples of groups represented by $R^a$, $R^b$, $R^c$, $R^e$, $R^f$, $R^g$, and $R^j$ include groups given as examples for the aforementioned titanium precursors.

Further, the thin-film-forming material of the present invention may include, as necessary, a nucleophilic reagent for imparting stability to the metal alkoxide compound of the present invention and the other precursors. Examples of such nucleophilic reagents include: ethylene glycol ethers, such as glyme, diglyme, triglyme, and tetraglyme; crown ethers, such as 18-crown-6, dicyclohexyl-18-crown-6, 24-crown-8, dicyclohexyl-24-crown-8, and dibenzo-24-crown-8; polyamines, such as ethylenediamine, N,N'-tetramethylethylenediamine, diethylenetriamine, triethylenetetramine, tetraethylene pentamine, pentaethylene hexamine, 1,1,4,7,7-pentamethyldiethylenetriamine, 1,1,4,7,10,10-hexamethyltriethylenetetramine, and triethoxytriethylene amine; cyclic polyamines, such as cyclam and cyclen; heterocycle compounds, such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; β-keto esters, such as methyl acetoacetate, ethyl acetoacetate, and 2-methoxyethyl acetoacetate; and β-diketones, such as acetylacetone, 2,4-hexane dione, 2,4-heptane dione, 3,5-heptane dione, and dipivaloylmethane. The amount of nucleophilic reagent(s) used with respect to 1 mol of the total amount of precursor(s) is preferably from 0.1 mol to 10 mol, and more preferably from 1 to 4 mol.

The thin-film-forming material of the present invention is made such that components, such as metal element impurities, halogen impurities such as chlorine impurities, and organic impurities, other than the components constituting the thin-film-forming material are excluded as much as possible. As for metal element impurities, the amount per element is preferably 100 ppb or less, more preferably 10 ppb or less, and the total amount is preferably 1 ppm or less, and more preferably 100 ppb or less. Particularly, in cases where the material is used for LSI gate insulating films, gate films, or barrier layers, it is necessary to minimize the content of alkali metal elements, alkaline-earth metal elements, and congeneric elements, which affect the electric characteristics of the obtained thin films. The amount of halogen impurities is preferably 100 ppm or less, and more preferably 10 ppm or less, and even more preferably 1 ppm or less. The total amount of organic impurities is preferably 500 ppm or less, more preferably 50 ppm or less, and even more preferably 10 ppm or less. Moisture causes the generation of particles in the chemical vapor deposition material and the generation of particles during the formation of a thin film, and thus, as for metal compounds, organic solvents, and nucleophilic reagents, it is better to remove as much moisture as possible in advance at the time of use in order to reduce the moisture in each component. The moisture content in each metal compound, organic solvent, or nucleophilic reagent is preferably 10 ppm or less, and more preferably 1 ppm or less.

Further, in order to reduce or prevent particle contamination of the thin film being formed, it is preferable that particles are excluded as much as possible from the thin-film-forming material of the present invention. More specifically, according to particle measurement by a light-scattering liquid-borne particle detector in a liquid phase, it is preferable that the number of particles larger than 0.3 μm is 100 or fewer in 1 ml of the liquid phase, and more preferably, the number of particles larger than 0.2 μm is 1000 or fewer in 1 ml of the liquid phase, and even more preferably, the number of particles larger than 0.2 μm is 100 or fewer in 1 ml of the liquid phase.

The thin-film production method of the present invention for producing a thin film by using a thin-film-forming material of the present invention follows the CVD method involving: introducing, into a deposition chamber in which a substrate is placed, a vapor obtained by vaporizing the thin-film-forming material of the present invention and a reactive gas which is used if necessary; and growing and depositing a metal-containing thin film on the surface of the substrate by decomposing and/or chemically reacting the precursor on the substrate. Generally known conditions and methods can be used without particularly limitation for the method for transporting/supplying the material, the deposition method, production conditions, the production device, etc.

Examples of the reactive gas which is used if necessary include: oxidizing gases, such as oxygen, ozone, nitrogen dioxide, nitric oxide, water vapor, hydrogen peroxide, formic acid, acetic acid, and acetic anhydride; reducing gases, such as hydrogen; and gases that produce a nitride, such as hydrazine, ammonia, and organic amine compounds such as monoalkylamine, dialkylamine, trialkylamine, and alkylene diamine. One or more types of gases may be used.

Examples of the transporting/supplying method include the gas transportation method, the liquid transportation method, the single-source method, and the cocktail-source method, as described above.

Examples of the deposition method include: thermal CVD in which a thin film is deposited by causing reaction of a material gas, or a material gas and a reactive gas, only by heat; plasma CVD that uses heat and a plasma; optical CVD that uses heat and light; optical plasma CVD that uses heat, light, and a plasma; and ALD in which the deposition reaction in CVD is divided into elementary processes, and deposition is performed stepwise on a molecular level.

Examples of the material for the substrate include: silicon; ceramics, such as silicon nitride, titanium nitride, tantalum nitride, titanium oxide, titanium nitride, ruthenium oxide, zirconium oxide, hafnium oxide, and lanthanum oxide; glass; and metals such as metallic ruthenium. The shape of the substrate may be, for example, plate-like, spherical, fibrous, or squamous. The surface of the substrate may be planar, or may have a three-dimensional structure such as a trench structure.

The aforementioned production conditions include, for example, reaction temperature (substrate temperature), reaction pressure, deposition rate, etc. The reaction temperature is preferably higher than or equal to 100° C., which is the temperature at which the metal alkoxide compound of the present invention reacts sufficiently, and is more preferably from 150° C. to 400° C. In cases of thermal CVD and optical CVD, the reaction pressure is preferably from atmospheric pressure to 10 Pa, and in cases of using a plasma, the reaction pressure is preferably from 2000 Pa to 10 Pa.

The deposition rate can be controlled by the material supplying conditions (vaporizing temperature, vaporizing pressure), the reaction temperature, and the reaction pressure. A high deposition rate may impair the characteristics of the obtained thin film, whereas a low deposition rate may cause problems in productivity. Thus, the deposition rate is preferably from 0.01 to 100 nm/minute, and more preferably from 1 to 50 nm/minute. In cases of ALD, the deposition rate is controlled by the number of cycles so that a desired film thickness can be obtained.

Other production conditions include the temperature and pressure at the time of vaporizing the thin-film-forming material into vapor. The step for vaporizing the thin-film-forming material into vapor may be performed inside the material container or inside the vaporizing chamber. In either case, it is preferable to evaporate the thin-film-forming material of the present invention at a temperature from 0 to 150° C. Further, in cases of vaporizing the thin-film-forming material into vapor inside the material container or the vaporizing chamber, the pressure inside the material container and the pressure inside the vaporizing chamber are both preferably from 1 to 10000 Pa.

The thin-film production method of the present invention employs ALD, and involves a material introduction step of vaporizing the thin-film-forming material into vapor and introducing the vapor into a deposition chamber according to the aforementioned transporting/supplying method, and may also involve: a precursor-thin-film deposition step of forming a precursor thin film on the surface of the substrate by the metal alkoxide compound in the vapor; a gas discharge step of discharging unreacted metal alkoxide compound gas; and a metal-containing-thin-film formation step of forming a metal-containing thin film on the surface of the substrate by chemically reacting the precursor thin film with a reactive gas.

Below, each of the aforementioned steps will be described in detail according to an example of forming a metal-oxide thin film. In cases of forming a metal-oxide thin film by ALD, first the aforementioned material introduction step is performed. The temperature and pressure preferred for making the thin-film-forming material into a vapor are as described above. Next, a precursor thin film is deposited on the substrate surface by the metal alkoxide compound introduced into a deposition reaction unit (precursor-thin-film deposition step). At this time, heat may be applied by heating the substrate or heating the deposition reaction unit. The precursor thin film deposited in this step is a metal-oxide thin film, or a thin film produced by the decomposition and/or reaction of a portion of the metal alkoxide compound, and has a different composition from the intended metal-oxide thin film. The substrate temperature during this step is preferably from room temperature to 500° C., and more preferably from 150 to 350° C. The pressure in the system (inside the deposition chamber) during this step is preferably from 1 to 10000 Pa, and more preferably from 10 to 1000 Pa.

Next, unreacted metal alkoxide compound gas and by-product gas are discharged from the deposition reaction unit (discharge step). It is ideal to completely discharge the unreacted metal alkoxide compound gas and by-product gas from the deposition reaction unit, but complete discharge is not absolutely necessary. Discharging methods include: purging the gases from the system by an inert gas such as nitrogen, helium, or argon; discharging the gases by depressurizing the inside of the system; and methods in which the above are combined. In cases of depressurization, the degree of depressurization is preferably from 0.01 to 300 Pa, and more preferably from 0.01 to 100 Pa.

Next, an oxidizing gas is introduced into the deposition reaction unit, and by the action of the oxidizing gas, or the oxidizing gas and heat, a metal-oxide thin film is formed from the precursor thin film obtained in the previous precursor-thin-film deposition step (metal-oxide-containing thin-film formation step). The temperature for causing the action of heat in the present step is preferably from room temperature to 500° C., and more preferably from 150 to 350° C. The pressure in the system (inside the deposition chamber) during this step is preferably from 1 to 10000 Pa, and more preferably from 10 to 1000 Pa. The metal alkoxide compound of the present invention has good reactivity with oxidizing gases, and can produce metal-oxide thin films.

In cases of employing ALD as described above in the thin-film production method of the present invention, thin-film deposition achieved by a series of operations—including the aforementioned material introduction step, precursor-thin-film deposition step, discharge step, and metal-oxide-containing thin-film formation step—is considered as a single cycle, and this cycle may be repeated a plurality of times until a thin film with the necessary film thickness is obtained. In this case, it is preferable that unreacted metal alkoxide compound gas, reactive gas (oxidizing gas in cases of forming a metal-oxide thin film), and by-product gas are discharged after each cycle as in the aforementioned discharge step, and then the next cycle is performed.

In the formation of metal-oxide thin films by ALD, energy such as plasma, light, or voltage may be applied, and also, a catalyst may be used. The timing for applying such energy and the timing for using the catalyst are not particularly limited, and for example, the timing may be: at the time of introducing a metal alkoxide compound gas in the material introduction step; at the time of heating in the precursor-thin-film deposition step or the metal-oxide-containing thin-film formation step; at the time of discharging gas from the system in the discharge step; at the time of introducing an oxidizing gas in the metal-oxide-containing thin-film formation step; or between the aforementioned steps.

Further, in the thin-film production method of the present invention, in order to obtain even better electric characteristics, it is possible to perform an annealing treatment in an inert atmosphere, an oxidizing atmosphere, or a reducing atmosphere, after thin-film deposition. In cases where steps need embedding, a reflow step may be provided; in this case, the temperature is from 200 to 1000° C., and preferably from 250 to 500° C.

A known chemical vapor deposition device can be used as the device for producing thin films by using the thin-film-forming material of the present invention. Concrete examples of such devices include: a device that can supply a precursor by bubbling, as illustrated in FIG. 1; a device having a vaporizing chamber, as illustrated in FIG. 2; and devices capable of subjecting a reactive gas to a plasma treatment, as illustrated in FIGS. 3 and 4. The device is not limited to single-substrate devices such as those illustrated in FIGS. 1, 2, 3, and 4, and it is possible to use a device that can simultaneously treat a plurality of substrates by using a batch furnace.

The thin film produced by using the thin-film-forming material of the present invention may be made as a desired type of thin film, such as metal, oxide ceramic, nitride ceramic, or glass, by appropriately selecting the other precursor(s), the reactive gas, and the production conditions. Such thin films are known to exhibit various characteristics, such as electric and optical characteristics, and are thus used for a variety of purposes. For example, copper and copper-containing thin films have the characteristics of high electroconductivity, high electromigration resistance, and high melting point, and are thus used as LSI wiring materials. Nickel and nickel-containing thin films are mainly used for electronic component members such as resistive films and barrier films, recording medium members such as magnetic films, and thin-film solar battery members such as electrodes. Cobalt and cobalt-containing thin films are used for electrode films, resistive films, adhesive films, magnetic tapes, carbide tool members, and the like.

An alcohol compound of the present invention is represented by the aforementioned general formula (II), and is a compound particularly suitable as a ligand in a compound that is suitable as a precursor in a thin-film production method involving a vaporizing step, such as CVD.

In the aforementioned general formula (II), $R^4$ represents a methyl group or an ethyl group, $R^5$ represents a hydrogen atom or a methyl group, and $R^6$ represents a $C_{1-3}$ linear or branched alkyl group. Examples of the $C_{1-3}$ linear or branched alkyl group represented by $R^6$ include a methyl group, an ethyl group, a propyl group, and an isopropyl group. Note, however, that if $R^5$ is a hydrogen atom, $R^4$ represents a methyl group or an ethyl group and $R^6$ represents a $C_{1-3}$ linear or branched alkyl group. If $R^5$ is a methyl group and $R^4$ is a methyl group, $R^6$ represents a $C_3$ linear or branched alkyl group. If $R^5$ is a methyl group and $R^4$ is an ethyl group, $R^6$ represents a $C_{1-3}$ linear or branched alkyl group.

The alcohol compound of the present invention may have optical isomers, but is not differentiated by optical isomerism.

Concrete examples of the alcohol compound of the present invention include the following Compounds Nos. 65 to 78.

[Chem. 14]

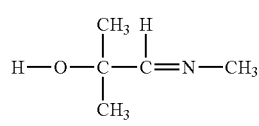

Compound No. 65

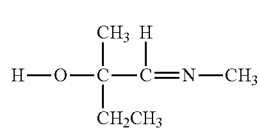

Compound No. 66

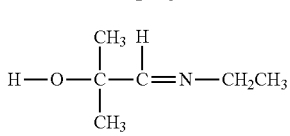

Compound No. 67

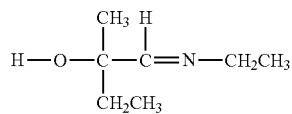

Compound No. 68

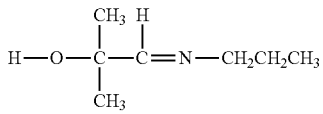

Compound No. 69

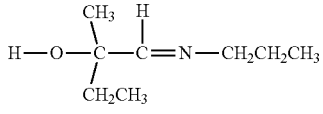

Compound No. 70

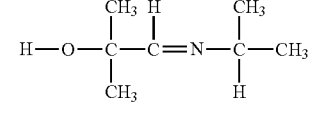

Compound No. 71

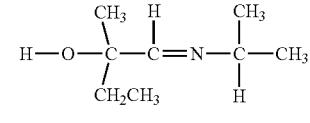

Compound No. 72

[Chem. 15]

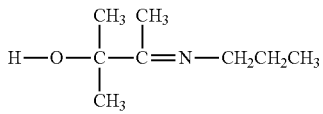

Compound No. 73

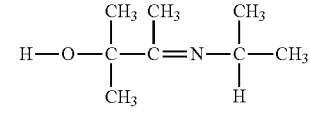

Compound No. 74

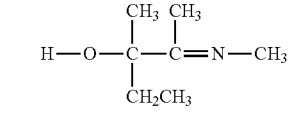

Compound No. 75

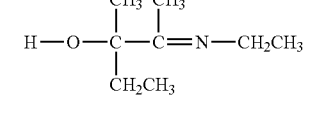

Compound No. 76

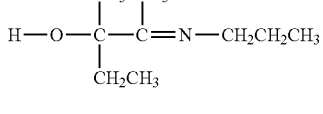

Compound No. 77

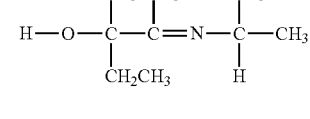

Compound No. 78

The alcohol compound of the present invention is not particularly limited by the production method thereof, and can be obtained, for example, by reacting an alkylene oxide compound, water, and an alkylamine compound under suitable conditions, performing extraction with a suitable solvent, and performing a dehydration treatment.

The alcohol compound of the present invention can be used as a ligand in a metal compound used as a thin-film-forming material or the like, and particularly, an alcohol compound wherein $R^5$ in the general formula (II) is hydrogen can be used as a ligand in a copper compound that is extremely useful as a material for forming a metallic-copper thin film. The alcohol compound of the present invention can also be used, for example, as synthetic materials for solvents, perfumes, agrochemicals, pharmaceuticals, and various polymers.

EXAMPLES

The present invention is described in further detail below according to working examples, production examples, comparative examples, and evaluation examples. The present invention, however, is not limited whatsoever by the following examples etc.

Examples 1 to 7 are production examples each for producing an alcohol compound of the present invention used as a material for a metal alkoxide compound of the present invention. Production Example 1 is an example for producing an alcohol compound used as a material for a metal alkoxide compound of the present invention. Examples 8 to 18 are production examples each for producing a metal alkoxide compound of the present invention.

Examples 19 and 20 are production examples each for producing a metallic-copper or copper-oxide thin film by using a metal alkoxide compound (copper compound) of the present invention. Comparative Example 1 is a production example for producing a metallic-copper thin film by using a comparative metal alkoxide compound (copper compound).

Evaluation Example 1 evaluates the physical properties (thermal stability) of metal alkoxide compounds of the present invention produced according to Examples 8 to 12 and of comparative compounds having structures similar to the present invention.

Evaluation Example 2 evaluates the physical properties (thermal stability) of metal alkoxide compounds (copper compounds) of the present invention produced according to Examples 13 to 15 and 17 and of a comparative compound having a structure similar to the present invention.

Evaluation Example 3 evaluates the physical properties of metallic-copper thin films produced according to Example 20 and Comparative Example 1.

Example 1

Production of Alcohol Compound (Compound No. 65) of Present Invention:

To a reaction flask were added 100 ml of diethyl ether and 45.5 g of 1-methoxy-2-methylpropylene oxide, and the mixture was stirred over an ice-cooled bath and cooled to around 0° C. Further, 50.0 g of water was added slowly dropwise over a period of 30 minutes, and the mixture was stirred for 15 minutes. Then, 45.0 g of a 40% methylamine aqueous solution was added slowly dropwise over a period of 30 minutes while cooling on ice, the mixture was stirred for 30 minutes, returned to room temperature, and subjected to reaction for about 20 hours. Then, extraction was performed with 300 ml of diethyl ether, and the obtained organic layer was subjected to a dehydration treatment by magnesium sulfate and a molecular sieve 4A. The molecular weight of the obtained compound was measured with a gas chromatograph mass spectrometer (may be abbreviated as GC-MS below). Also, an elementary analysis of the obtained compound was performed. These analysis values are indicated in (1) and (2) below. From these results, it was verified that the obtained compound was Compound No. 65. Note that the yield of the compound was 45%.

Analysis Values:
(1) GC-MS m/z: 101 (M+)
(2) Elementary Analysis: C: 59.0 mass %; H: 11.5 mass %; O: 15.2 mass %; N: 14.3 mass % (theoretical values: C: 59.4%; H: 10.9%; O: 15.8%; N: 13.9%).

Example 2

Production of Alcohol Compound (Compound No. 66) of Present Invention:

To a reaction flask was added 20.0 g of 1,1-dimethoxy-2-methylbutane-2-ol, and a solution made by mixing 20 g of water and 0.8 ml of a 36% hydrochloric acid was added slowly dropwise to the reaction flask over a period of 30 minutes at room temperature, and the mixture was stirred for about 60 hours. Then, 31.4 g of a 40% methylamine aqueous solution was added slowly dropwise over a period of 30 minutes while cooling on ice, the mixture was returned to room temperature, and was subjected to reaction for 3 hours. Then, extraction was performed with 80 ml of toluene, and the obtained organic layer was subjected to a dehydration treatment with magnesium sulfate and a molecular sieve 4A. The molecular weight of the obtained compound was measured with a GC-MS. Also, an elementary analysis of the obtained compound was performed. These analysis values are indicated in (1) and (2) below. From these results, it was verified that the obtained compound was Compound No. 66. Note that the yield of the compound was 54%.

Analysis Values:
(1) GC-MS m/z: 115 (M+)
(2) Elementary Analysis: C: 63.0 mass %; H: 10.8 mass %; O: 13.5 mass %; N: 12.6 mass % (theoretical values: C: 62.6%; H: 11.3%; O: 13.9%; N: 12.2%).

Example 3

Production of Alcohol Compound (Compound No. 67) of Present Invention:

To a reaction flask were added 30 g of diethyl ether and 2.5 g of water, and the mixture was stirred over an ice-cooled bath and cooled to around 0° C. Then, 2.5 g of 1-methoxy-2-methylpropylene oxide was added slowly dropwise to the reaction flask over a period of 5 minutes, and the mixture was stirred for 15 minutes. Then, 4.4 g of a 33% ethylamine aqueous solution was added slowly dropwise over a period of 10 minutes while cooling on ice, the mixture was stirred for 30 minutes, returned to room temperature, and subjected to reaction for about 20 hours. Then, extraction was performed with 50 ml of diethyl ether, and the obtained organic layer was subjected to a dehydration treatment with magnesium sulfate and a molecular sieve 4A. The molecular weight of the obtained compound was measured with a GC-MS. Also, an elementary analysis of the obtained compound was performed. These analysis values are indicated in (1) and (2) below. From these results, it was verified that the obtained compound was Compound No. 67. Note that the yield of the compound was 52%.

Analysis Values:
(1) GC-MS m/z: 115 (M+)
(2) Elementary Analysis: C: 62.9 mass %; H: 11.0 mass %; O: 14.6 mass %; N: 11.9 mass % (theoretical values: C: 62.6%; H: 11.3%; O: 13.9%; N: 12.2%).

Example 4

Production of Alcohol Compound (Compound No. 71) of Present Invention:

In a reaction flask, a mixed solution of 30 g of diethyl ether and 2.5 g of water was stirred while cooling on ice, and the solution temperature was cooled to 10° C. To this reaction flask, 2.5 g of 1-methoxy-2-methylpropylene oxide was added dropwise at the same temperature, and the mixture was stirred for 30 minutes. Then, isopropylamine was added dropwise at the same temperature while cooling on ice, and the mixture was stirred for 30 minutes. Then, the mixture was returned to room temperature and stirred for 8 hours. A suitable amount of magnesium sulfate was added to adsorb the water in the solution, and the solution was filtered. A sufficiently dried molecular sieve 4A was added to the filtrate to completely dehydrate the filtrate. The molecular weight of the obtained compound was measured with a GC-MS. Also, an elementary analysis of the obtained compound was performed. These analysis values are indicated in (1) and (2) below. From these results, it was verified that the obtained compound was Compound No. 71. Note that the yield of the compound was 51%.

Analysis Values:
(1) GC-MS m/z: 129 (M+)
(2) Elementary Analysis: C: 64.8 mass %; H: 11.3 mass %; O: 12.9 mass %; N: 11.2 mass % (theoretical values: C: 65.1%; H: 11.6%; O: 12.4%; N: 10.9%).

Example 5

Production of Alcohol Compound (Compound No. 74) of Present Invention:

To a reaction flask were added 27.1 g of 3-hydroxy-3-methyl-2-butanone, 33.1 g of methanol, and a molecular sieve 4A, and the mixture was stirred at room temperature. To this reaction flask, 23.2 g of isopropylamine was added slowly dropwise at room temperature. After completion of this dropwise addition, the mixture was stirred for 6 hours at room temperature. Then, stirring was stopped, 7.93 g of a molecular sieve 4A was added, and the mixture was left still for 15 hours at room temperature. Then, the mixture was filtered, and the filtrate was fractionated. Methanol was removed by evaporation from the fractionated filtrate. The liquid residue was distilled under reduced pressure at a pressure of 3.8 kPa and a fraction temperature of 62° C. The yielded amount of the obtained compound was 10.4 g, and the yield was 27%. The molecular weight of the obtained compound was measured with a GC-MS. Further, $^1$H-NMR of the obtained compound was measured, and elementary analysis was performed. These analysis values are indicated in (1), (2), and (3) below. From these results, it was verified that the obtained compound was Compound No. 74.

Analysis Values:
(1) $^1$H-NMR (solvent: deuterated benzene) (chemical shift: multiplicity: number of H): (5.996:t:1), (3.332:m: 1), (1.329:t:3), (1.232:s:6), (0.967:d:6).
(2) GC-MS m/z: 144 (M+)
(3) Elementary Analysis: C: 67.6 mass %; H: 12.3 mass %; O: 10.8 mass %; N: 9.5 mass % (theoretical values: C: 67.1%; H: 11.9%; O: 11.2%; N: 9.8%).

Example 6

Production of Alcohol Compound (Compound No. 68) of Present Invention:

To a reaction flask was added a tetrahydrofuran solution of ethylmagnesium bromide (7.4%, 440 g), and this was stirred over an ice-cooled bath and cooled to around 0° C. To this solution, pyruvic aldehyde dimethylacetal (30 g) was added dropwise over a period of 30 minutes, and the solution was subjected to a Grignard reaction. Then, the solution was returned to room temperature, and was subjected to reaction for 12 hours. The reaction solution was cooled on ice and was quenched by adding dropwise 300 g of a 17% ammonium chloride aqueous solution, and then, the solution was transferred to a separatory funnel to separate organic matters, and was dehydrated with a suitable amount of magnesium sulfate. After filtering the organic layer, this was desolventized at around 80° C. in an oil bath under reduced pressure. Then, distillation was performed in an oil bath at around 85° C. under reduced pressure, and at a column top temperature of 49° C., 20 g of colorless, transparent 1,1-dimethoxy-2-methylbutane-2-ol was obtained. To 20 g of this 1,1-dimethoxymethylbutane-2-ol, 40 g of pure water and 2.5 g of a 36% hydrochloric acid were added while cooling on ice, and the mixture was stirred overnight. Then, 74 g of a 33% ethylamine aqueous solution was added dropwise while cooling on ice, and the mixture was subjected to reaction for 10 hours. At this time, the pH of the reaction solution was from 10 to 11. In order to recover the target product dissolved in the aqueous solution, 150 g of toluene was added to the reaction solution, and the organic layer was extracted and separated with a separatory funnel, was dehydrated with magnesium sulfate, and was filtered. Then, in an oil bath at 90° C. under reduced pressure, the toluene was removed. The yielded amount of the obtained compound was 7.9 g, and the yield was 45%. The molecular weight of the obtained compound was measured with a GC-MS. Further, $^1$H-NMR of the obtained compound was measured. These analysis values are indicated in (1) and (2) below. From these results, it was verified that the obtained compound was Compound No. 68.

Analysis Values:
(1) GC-MS m/z: 129 (M+)
(2) $^1$NMR (solvent: deuterated benzene) (chemical shift: multiplicity: number of H):
(7.116:s:1), (4.413:s:1), (3.153-3.193:m:2), (1.501-1.573: m:1), (1.347-1.419:m:1), (1.152:s:3), (0.981-1.017:t:3), (0.837-0.875:t:3).

Example 7

Production of Alcohol Compound (Compound No. 76) of Present Invention:

To a reaction flask was added a diethyl ether solution of ethylmagnesium bromide (39%, 16 g), and this was stirred over an ice-cooled bath and cooled to around 0° C. To this solution, 3,3-dimethoxy-2-butanone (6.19 g) was added dropwise in 1 hour, and the solution was subjected to a Grignard reaction. Then, the solution was returned to room temperature, and was subjected to reaction for 12 hours. The reaction solution was cooled on ice, and then 75 g of a 20% ammonium chloride aqueous solution was added dropwise, and then 3 ml of a 36% hydrochloric acid solution was added dropwise, and the mixture was stirred overnight. Only the organic layer was separated and recovered, and then 18.5 g of a 33% ethylamine aqueous solution was added thereto dropwise while cooling on ice, and the mixture was subjected to reaction for 20 hours. At this time, the pH of the reaction solution was from 10 to 11. The reaction solution was dehydrated by adding magnesium sulfate and was filtered, and then desolventization was performed in an oil bath at 60° C. under reduced pressure. Distillation was performed in an oil bath at 80° C. at a pressure of 300 Pa. The obtained compound was a colorless transparent liquid, and the yielded amount was 2.3 g, and the yield was 34%. The molecular weight of the obtained compound was measured with a GC-MS. Further, $^1$H-NMR of the obtained compound was measured. These analysis values are indicated in (1) and (2) below. From these results, it was verified that the obtained compound was Compound No. 76.

Analysis Values:
(1) GC-MS m/z: 143.23 (M+)
(2) $^1$NMR (solvent: deuterated benzene) (chemical shift: multiplicity: number of H):
(5.85:s:1), (2.948-3.003:q:2), (1.602-1.692:m:1), (1.379-1.475:m:1), (1.254:s:3), (1.223:s:3), (1.040-1.077:t:3), (0.826-0.863:t:3).

Production Example 1

Production of Alcohol Compound 1:
In a reaction flask, a tetrahydrofuran solution of methylamine (2 M, 200 ml) was cooled on ice, and 24 g of 3-hydroxy-3-methyl-2-butanone was added thereto dropwise, and the mixture was subjected to reaction at a liquid temperature of around 10° C. Then, the mixture was returned to room temperature and was stirred for 8 hours. A suitable amount of magnesium sulfate was added to adsorb the water in the solution, and the solution was filtered. A sufficiently dried molecular sieve 4A was added to the filtrate to completely dehydrate the filtrate. The molecular weight of the obtained compound was measured with a GC-MS. Also, an elementary analysis of the obtained compound was performed. These analysis values are indicated in (1) and (2) below. From these results, it was verified that the obtained compound was the following alcohol compound 1. Note that the yield of the compound was 49%.

Analysis Values:
(1) GC-MS m/z: 115 (M+)
(2) Elementary Analysis: C: 61.7 mass %; H: 11.3 mass %; O: 13.9 mass %; N: 12.2 mass % (theoretical values: C: 62.6%; H: 11.3%; O: 13.9%; N: 12.2%).

[Chem. 16]

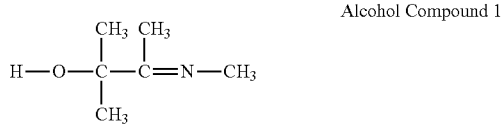

Alcohol Compound 1

Example 8

Production of Metal Alkoxide Compound (Compound No. 25) of Present Invention:
To a reaction flask were added 1.2 g of copper (II) methoxide and 20 g of dehydrated toluene and these were made into a suspension. To this suspension, 18 g of a 15 wt. % tetrahydrofuran solution of the alcohol compound 1 obtained in Production Example 1 was added dropwise at room temperature in an argon gas atmosphere. After stirring for 1 hour, the solution gradually turned purple, and was kept stirred at room temperature for 10 hours. Then, the tetrahydrofuran was removed by evaporation in an oil bath at a temperature of 85° C., and then, solvents such as toluene were removed by evaporation in an oil bath at a temperature of 120° C. under slightly reduced pressure. The obtained purple solid was sublimed at 110° C. at 40 Pa, to obtain the target product. The obtained compound was a solid having a melting point of 195° C. The yield of the compound was 50%. The obtained compound was a compound exhibiting no spontaneous ignitability. The obtained compound was subjected to single-crystal X-ray structural analysis. FIG. 5 illustrates a molecular structure diagram obtained by the single-crystal X-ray structural analysis. From this result, it was verified that the obtained compound was Compound No. 25. Further, the obtained compound was subjected to TG-DTA measurement under atmospheric pressure or under reduced pressure. These analysis values are indicated in (1) and (2) below.

Analysis Values:
(1) Atmospheric Pressure TG-DTA
50% mass reduction temperature: 205° C. (Ar flow rate: 100 ml/min.; temperature rise: 10° C./min.)
(2) Reduced Pressure TG-DTA
50% mass reduction temperature: 154° C. (pressure: 10 Torr; Ar flow rate: 50 ml/min.; temperature rise: 10° C./min.)

Example 9

Production of Metal Alkoxide Compound (Compound No. 41) of Present Invention:
To a reaction flask were added 6.01 g of hexaamminenickel (II) chloride and 39.00 g of tetrahydrofuran, and the mixture was stirred at room temperature. To this mixture was added dropwise, at room temperature, a solution in which 7.30 g of a sodium alkoxide obtained by reacting sodium and the alcohol compound 1, which was obtained in Production Example 1, was suspended in 24 g of tetrahydrofuran. After completion of this dropwise addition, the solution was stirred at room temperature for 2 hours, and was then refluxed for 7 hours. Then, the solution was left to cool at room temperature, was then stirred for 15 hours, and was filtered. Tetrahydrofuran was removed from the obtained filtrate, and a green solid was obtained as the residue. The solid was sublimed under the conditions of 100 Pa and 120° C. The yielded amount of the obtained compound was 0.98 g, and the yield was 13%. The obtained compound was a green solid having a melting point of 212° C. The obtained compound was a compound exhibiting no spontaneous ignitability. The obtained compound was subjected to single-crystal X-ray structural analysis. FIG. 6 illustrates a molecular structure diagram obtained by the single-crystal X-ray structural analysis. From this result, it was verified that the obtained compound was Compound No. 41. Further, the obtained compound was subjected to $^1$H-NMR and TG-DTA measurement under atmospheric pressure or under reduced pressure. These analysis values are indicated in (1), (2), and (3) below.

Analysis Values:
(1) $^1$H-NMR (solvent: deuterated benzene) (chemical shift: multiplicity: number of H):
(2.425:s:6), (1.246:s:12), (0.955:s:6).
(2) Atmospheric Pressure TG-DTA
50% mass reduction temperature: 218° C. (Ar flow rate: 100 ml/min.; temperature rise: 10° C./min.)
(3) Reduced Pressure TG-DTA
50% mass reduction temperature: 160° C. (pressure: 10 Torr; Ar flow rate: 50 ml/min.; temperature rise: 10° C./min.)

Example 10

Production of Metal Alkoxide Compound (Compound No. 47) of Present Invention:
In a reaction flask were placed 5.08 g of hexaamminenickel (II) chloride and 15 g of tetrahydrofuran, and the mixture was stirred at room temperature. To this mixture was added dropwise, at room temperature, a solution in which 7.10 g of a sodium alkoxide obtained by reacting sodium and Compound No. 74, which was obtained in Example 5, was suspended in 17 g of tetrahydrofuran. After completion of this dropwise addition, the solution was stirred at room temperature for 20 minutes, and was then refluxed for 5 hours. Then, the solution was left to cool at room temperature, was then stirred for 15 hours, and was filtered. Tetrahydrofuran was removed from the obtained filtrate, and a green solid was obtained as the residue. The solid was sublimed under the conditions of 100 Pa and 100° C. The yielded amount of the obtained compound was 4.87 g, and the yield was 65%. The obtained compound was a blackish-brownish solid having a melting point of 155° C. The obtained compound was a compound exhibiting no spontaneous ignitability. The obtained compound was subjected to single-crystal X-ray structural analysis. FIG. 7 illustrates a molecular structure diagram obtained by the single-crystal X-ray structural analysis. From this result, it was verified that the obtained compound was Compound No. 47. Further, the obtained compound was subjected to $^1$H-NMR and TG-DTA measurement under atmospheric pressure or under reduced pressure. These analysis values are indicated in (1), (2), and (3) below.

Analysis Values:

(1) $^1$H-NMR (solvent: deuterated benzene) (chemical shift: multiplicity: number of H):

(3.774:sept:2), (1.444:d:12), (1.184:s:12), (1.060:s:6).

(2) Atmospheric Pressure TG-DTA

50% mass reduction temperature: 203° C. (Ar flow rate: 100 ml/min.; temperature rise: 10° C./min.)

(3) Reduced Pressure TG-DTA

50% mass reduction temperature: 140° C. (pressure: 10 Torr; Ar flow rate: 50 ml/min.; temperature rise: 10° C./min.)

Example 11

Production of Metal Alkoxide Compound (Compound No. 57) of Present Invention:

In a reaction flask were placed 3.50 g of cobalt (II) chloride and 20 g of tetrahydrofuran, and the mixture was stirred at room temperature. To this mixture was added dropwise, at room temperature, a solution in which 7.11 g of a sodium alkoxide obtained by reacting sodium and the alcohol compound 1, which was obtained in Production Example 1, was suspended in 10 g of tetrahydrofuran. After completion of this dropwise addition, the solution was stirred for 23 hours at room temperature, and was filtered. Tetrahydrofuran was removed from the obtained filtrate, and a dark brown solid was obtained as the residue. The solid was sublimed under the conditions of 80 Pa and 145° C. The yielded amount of the obtained compound was 0.91 g, and the yield was 13%. The obtained compound was an orange solid having a melting point of 220° C. The obtained compound was a compound exhibiting no spontaneous ignitability. The obtained compound was subjected to single-crystal X-ray structural analysis. FIG. 8 illustrates a molecular structure diagram obtained by the single-crystal X-ray structural analysis. From this result, it was verified that the obtained compound was Compound No. 57. Further, the obtained compound was subjected to TG-DTA measurement under atmospheric pressure or under reduced pressure. These analysis values are indicated in (1) and (2) below.

Analysis Values:

(1) Atmospheric Pressure TG-DTA

50% mass reduction temperature: 219° C. (Ar flow rate: 100 ml/min.; temperature rise: 10° C./min.)

(2) Reduced Pressure TG-DTA

50% mass reduction temperature: 166° C. (pressure: 10 Torr; Ar flow rate: 50 ml/min.; temperature rise: 10° C./min.)

Example 12

Production of Metal Alkoxide Compound (Compound No. 63) of Present Invention:

In a 200-ml four-neck flask were placed 2.79 g of cobalt (II) chloride and 22 g of tetrahydrofuran, and the mixture was stirred at room temperature. To this mixture was added dropwise, at room temperature, a solution in which 6.46 g of a sodium alkoxide obtained by reacting sodium and Compound No. 74, which was obtained in Example 5, was suspended in 10 g of tetrahydrofuran. After completion of this dropwise addition, the solution was stirred for 22 hours at room temperature, and was filtered. Tetrahydrofuran was removed from the obtained filtrate, and a green solid was obtained as the residue. This solid was sublimed under the conditions of 80 Pa and 100° C. The yielded amount of the obtained compound was 2.24 g, and the yield was 34%. The obtained compound was a green solid having a melting point of 145° C. The obtained compound was a compound exhibiting no spontaneous ignitability. The obtained compound was subjected to single-crystal X-ray structural analysis. FIG. 9 illustrates a molecular structure diagram obtained by the single-crystal X-ray structural analysis. From this result, it was verified that the obtained compound was Compound No. 63. The obtained compound was subjected to TG-DTA measurement under atmospheric pressure or under reduced pressure. These analysis values are indicated in (1) and (2) below.

Analysis Values:

(1) Atmospheric Pressure TG-DTA

50% mass reduction temperature: 227° C. (Ar flow rate: 100 ml/min.; temperature rise: 10° C./min.)

(2) Reduced Pressure TG-DTA

50% mass reduction temperature: 149° C. (pressure: 10 Torr; Ar flow rate: 50 ml/min.; temperature rise: 10° C./min.)

Evaluation Example 1

Evaluation of Physical Properties of Alkoxide Compound:

For each of Compounds Nos. 25, 41, 47, 57, and 63 of the present invention obtained in Examples 8-12 and the following Comparative Compounds 1, 2, and 3, the temperature at which the sample weight was reduced by 50 mass % by heating in a reduced-pressure atmosphere (10 torr) was verified by using a TG-DTA measurement device (this temperature may be abbreviated below as TG 50% reduction temperature). Further, by measuring the temperature at which thermal decomposition occurs by using a DSC measurement device, the thermal stability of each compound was verified. The results are shown in Table 1.

[Chem. 16]

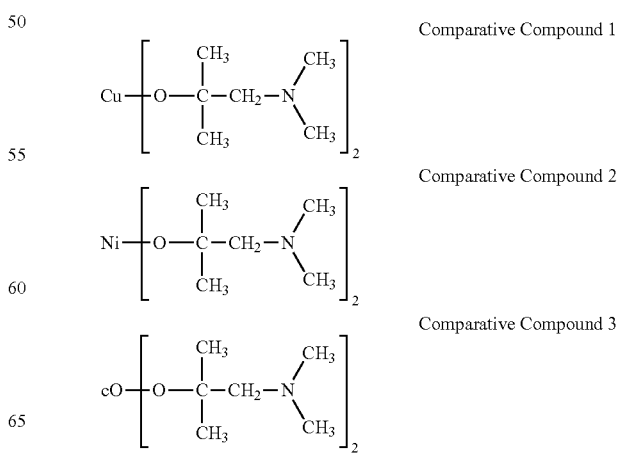

TABLE 1

| Evaluation Example | Compound | TG 50% reduction temperature (° C.) | Thermal decomposition occurrence temperature (° C.) |
|---|---|---|---|
| Comp. Evaluation Example 1-1 | Comp. Compound 1 | 165 | 210 |
| Comp. Evaluation Example 1-2 | Comp. Compound 2 | 110 | 290 |
| Comp. Evaluation Example 1-3 | Comp. Compound 3 | 155 | 220 |
| Evaluation Example 1-1 | Compound No. 25 | 150 | 230 |
| Evaluation Example 1-2 | Compound No. 41 | 160 | 330 |
| Evaluation Example 1-3 | Compound No. 47 | 140 | 320 |
| Evaluation Example 1-4 | Compound No. 57 | 165 | 290 |
| Evaluation Example 1-5 | Compound No. 63 | 150 | 300 |

From the results in Table 1, when Compound No. 25 was compared with Comparative Compound 1 which is a copper tertiary-aminoalkoxide compound having a similar structure, it was found that Compound No. 25 had a low TG 50% reduction temperature and a high thermal decomposition temperature. When Compounds Nos. 41 and 47 were compared with Comparative Compound 2 which is a nickel tertiary-aminoalkoxide compound having a similar structure, it was found that Compounds Nos. 41 and 47 had significantly-improved thermal decomposition temperatures that greatly exceeded 300° C., although Comparative Compound 2 had a slightly lower TG 50% reduction temperature. When Compounds Nos. 57 and 63 were compared with Comparative Compound 3 which is a cobalt tertiary-aminoalkoxide compound having a similar structure, it was found that Compounds Nos. 57 and 63 had significantly-improved thermal decomposition temperatures, although there was no significant difference in TG 50% reduction temperature. From the above, it was found that the compounds of the present invention have vapor pressures that are the same as or higher than conventional products and also have higher thermal decomposition temperatures, and are thus particularly suitable as CVD materials.

Example 13

Production of Metal Alkoxide Compound (Compound No. 17) of Present Invention:

In an argon gas atmosphere, a mixed solution of Compound No. 65 obtained in Example 1 and 400 ml of diethyl ether was added slowly dropwise to 7.45 g of copper (II) methoxide while cooling on ice. Then, the solution was returned to room temperature, and was subjected to reaction for about 17 hours. Then, diethyl ether was removed by evaporation in a bath at 58° C. under atmospheric pressure, to obtain a dark purple crystal. Then, 350 ml of hexane was added and the mixture was heated in a bath at 56° C., to dissolve the crystal. The obtained solution was thermally filtered with a 0.2-μm membrane filter, and was recrystallized, to obtain a dark purple crystal. The recovery rate by this refinement was 37%. The obtained compound was a solid having a melting point of 165° C. The obtained compound was a compound exhibiting no spontaneous ignitability. The obtained compound was subjected to single-crystal X-ray structural analysis. FIG. 10 illustrates a molecular structure diagram obtained by the single-crystal X-ray structural analysis. From this result, it was verified that the obtained compound was Compound No. 17. Further, the obtained compound was subjected to TG-DTA measurement under atmospheric pressure or under reduced pressure. These analysis values are indicated in (1) and (2) below.

Analysis Values:
(1) Atmospheric Pressure TG-DTA
50% mass reduction temperature: 173° C. (Ar flow rate: 100 ml/min.; temperature rise: 10° C./min.)
(2) Reduced Pressure TG-DTA
50% mass reduction temperature: 121° C. (pressure: 10 Torr; Ar flow rate: 50 ml/min.; temperature rise: 10° C./min.)

Example 14

Production of Metal Alkoxide Compound (Compound No. 18) of Present Invention:

In an argon gas atmosphere, a mixed solution of Compound No. 66 obtained in Example 2 and 80 ml of toluene was added slowly dropwise to 1.60 g of copper (II) methoxide while cooling on ice. Then, the solution was returned to room temperature, and was subjected to reaction for about 20 hours. Then, toluene was removed by evaporation under reduced pressure in a bath at 94° C., to obtain a dark purple crystal. This solid was sublimed under reduced pressure at 83° C. in a glass tube oven, to obtain a purple crystal. The obtained compound was a solid having a melting point of 103° C. The yield of the obtained compound was 43%. The obtained compound was a compound exhibiting no spontaneous ignitability. The obtained compound was subjected to single-crystal X-ray structural analysis. FIG. 11 illustrates a molecular structure diagram obtained by the single-crystal X-ray structural analysis. From this result, it was verified that the obtained compound was Compound No. 18. Further, the obtained compound was subjected to TG-DTA measurement under atmospheric pressure or under reduced pressure. These analysis values are indicated in (1) and (2) below.

Analysis Values:
(1) Atmospheric Pressure TG-DTA
50% mass reduction temperature: 169° C. (Ar flow rate: 100 ml/min.; temperature rise: 10° C./min.)
(2) Reduced Pressure TG-DTA
50% mass reduction temperature: 116° C. (pressure: 10 Torr; Ar flow rate: 50 ml/min.; temperature rise: 10° C./min.)

Example 15

Production of Metal Alkoxide Compound (Compound No. 19) of Present Invention:

In an argon gas atmosphere, a mixed solution of Compound No. 67 obtained in Example 3 and 50 ml of diethyl ether was added slowly dropwise, while cooling on ice, to a mixed solution of 0.65 g of copper (II) methoxide and 30 ml of hexane. Then, the solution was returned to room temperature, and was subjected to reaction for about 16 hours. Then, diethyl ether was removed by evaporation in a bath at 70° C. under atmospheric pressure, to obtain a dark purple crystal. This solid was sublimed under reduced pressure at 83° C. in a glass tube oven, to obtain a purple crystal. The yield of the obtained compound was 38%. The obtained compound was a compound exhibiting no spontaneous ignitability. The obtained compound was subjected to single-crystal X-ray structural analysis. FIG. 12 illustrates a molecular structure diagram obtained by the single-crystal X-ray structural analysis. From this result, it was verified that the obtained compound was Compound No. 19. Further, the obtained compound was subjected to TG-DTA measurement under atmospheric pressure or under reduced pressure. These analysis values are indicated in (1) and (2) below.

Analysis Values:

(1) Atmospheric Pressure TG-DTA

50% mass reduction temperature: 170° C. (Ar flow rate: 100 ml/min.; temperature rise: 10° C./min.)

(2) Reduced Pressure TG-DTA

50% mass reduction temperature: 116° C. (pressure: 10 Torr; Ar flow rate: 50 ml/min.; temperature rise: 10° C./min.)

Example 16

Production of Metal Alkoxide Compound (Compound No. 20) of Present Invention:

In an argon gas atmosphere, 42 g of a 4.24 wt. % toluene solution of Compound No. 68, which was obtained in Example 6, was added dropwise to 0.786 g of copper (II) methoxide. The solute dissolved immediately and exhibited a purple color, but the solution was kept stirred at room temperature for 17 hours. Toluene was removed by evaporation in an oil bath at a temperature of 70° C. under slightly reduced pressure, and then, the remaining toluene was completely removed by evaporation in an oil bath at a temperature of 90° C. under reduced pressure. The obtained purple solid was distilled at 100° C. at 40 Pa, to obtain the target product. The obtained compound was a solid having a melting point of 58° C. The yield of the compound was 48%. The obtained compound was subjected to single-crystal X-ray structural analysis. FIG. 13 illustrates a molecular structure obtained by the single-crystal X-ray structural analysis. From this result, it was verified that the obtained compound was Compound No. 20. Further, the obtained compound was subjected to TG-DTA measurement under atmospheric pressure or under reduced pressure, and to DSC measurement. These analysis values are indicated in (1), (2), and (3) below.

Analysis Values:

(1) Atmospheric Pressure TG-DTA

50% mass reduction temperature: 174° C. (Ar flow rate: 100 ml/min.; temperature rise: 10° C./min.)

(2) Reduced Pressure TG-DTA

50% mass reduction temperature: 108° C. (pressure: 10 Torr; Ar flow rate: 50 ml/min.; temperature rise: 10° C./min.)

(3) DSC Thermal Decomposition Occurrence Temperature

168° C.

Example 17

Production of Metal Alkoxide Compound (Compound No. 23) of Present Invention:

In a 100-ml three-neck flask, 20 g of a 15 wt. % ether solution of Compound No. 71, which was obtained in Example 4, was added dropwise, at room temperature in an argon gas atmosphere, to a suspension of 1.2 g of copper (II) methoxide and 20 g of dehydrated hexane. After stirring for 1 hour, the solution gradually exhibited a purple color, and the solution was kept stirred for 10 hours at room temperature. Ether was removed by evaporation in a bath at 50-60° C., and then solvents, such as hexane, were removed by evaporation in a bath at 110° C. The residue was sublimed at 110° C. at 40 Pa. The obtained compound was a solid having a melting point of 185° C. The yield was 40%. The obtained compound was a compound exhibiting no spontaneous ignitability. The obtained compound was subjected to single-crystal X-ray structural analysis. FIG. 14 illustrates a molecular structure diagram obtained by the single-crystal X-ray structural analysis. From this result, it was verified that the obtained compound was Compound No. 23. Further, the obtained compound was subjected to TG-DTA measurement under atmospheric pressure or under reduced pressure. These analysis values are indicated in (1) and (2) below.

Analysis Values:

(1) Atmospheric Pressure TG-DTA

50% mass reduction temperature: 184° C. (Ar flow rate: 100 ml/min.; temperature rise: 10° C./min.)

(2) Reduced Pressure TG-DTA

50% mass reduction temperature: 131° C. (pressure: 10 Torr; Ar flow rate: 50 ml/min.; temperature rise: 10° C./min.)

Example 18

Production of Metal Alkoxide Compound (Compound No. 60) of Present Invention:

To a reaction flask were added 1.15 g of cobalt-bis-trimethylsilylamide and 20 g of dehydrated toluene, and the mixture was mixed sufficiently. This solution was cooled on ice, and 1.05 g of 2-ethylimino-3-methylpentane-3-ol was added dropwise over a period of 5 minutes. The solution changed from dark blue to brown. After completion of this dropwise addition, the solution was stirred overnight at room temperature. Then, the solution was desolventized under reduced pressure in an oil bath at 100° C., and the produced cobalt complex (brown solid) was sufficiently dried. This cobalt complex was placed in a 50-ml flask which was connected to a sublimation refinement device. Sublimation refinement was performed in an oil bath at 100-110° C. at 40 Pa, to obtain 0.50 g of a red-brown crystal. The yield of the compound was 53%. The melting point of the obtained solid was 104° C. FIG. 15 illustrates a result of the single-crystal X-ray structural analysis. From this result, it was verified that the obtained compound was Compound No. 60. Further, the obtained compound was subjected to TG-DTA measurement under atmospheric pressure or under reduced pressure, and to DSC measurement. These analysis values are indicated in (1), (2), and (3) below.

Analysis Values:

(1) Atmospheric Pressure TG-DTA

50% mass reduction temperature: 211.9° C. (Ar flow rate: 100 ml/min.; temperature rise: 10° C./min.)

(2) Reduced Pressure TG-DTA

50% mass reduction temperature: 128.8° C. (pressure: 10 Torr; Ar flow rate: 50 ml/min.; temperature rise: 10° C./min.)

(3) DSC Thermal Decomposition Occurrence Temperature

315° C.

Evaluation Example 2

Evaluation of Physical Properties of Alkoxide Compound:

For each of Compounds Nos. 17, 18, 19, and 23, which are copper alkoxide compounds of the present invention obtained in Examples 13 to 15 and 17, and Comparative Compound 1, the temperature at which the sample weight was reduced by 50 mass % by heating in a reduced-pressure atmosphere (10 torr) was verified by using a TG-DTA measurement device. Further, by measuring the temperature at which thermal decomposition occurs by using a DSC measurement device, the thermal stability of each compound was verified. The results are shown in Table 2.

TABLE 2

| Evaluation Example | Compound | TG 50% reduction temperature (° C.) | Thermal decomposition occurrence temperature (° C.) |
|---|---|---|---|
| Comp. Evaluation Example 2 | Comp. Compound 1 | 165 | 210 |
| Evaluation Example 2-1 | Compound No. 17 | 120 | 160 |
| Evaluation Example 2-2 | Compound No. 18 | 115 | 170 |
| Evaluation Example 2-3 | Compound No. 19 | 115 | 170 |
| Evaluation Example 2-4 | Compound No. 23 | 130 | 190 |

From the results in Table 2, when Compounds Nos. 17 to 19 and 23 (Evaluation Examples 2-1 to 2-4) were compared with Comparative Compound 1 (Comparative Evaluation Example 2) having a similar structure, it was found that Compounds Nos. 17 to 19 and 23 had significantly lower TG 50% reduction temperatures than Comparative Compound 1. Further, it was found that Compounds Nos. 17 to 19 and 23 had thermal decomposition occurrence temperatures below 200° C., whereas the thermal decomposition occurrence temperature of Comparative Compound 1 was above 200° C.

From the above, it was found that the copper compounds of the present invention are particularly suitable as materials for forming metallic-copper thin films by CVD.

Example 19

Production of Copper-Oxide Thin Film:

The copper compound (Compound No. 18) of the present invention obtained in Example 14 was used as a chemical vapor deposition material, and a copper-oxide thin film was produced on a silicon wafer substrate by CVD according the following conditions by using the device illustrated in FIG. 3. The obtained thin film was subjected to film-thickness measurement by X-ray reflectometry and to a verification of thin-film structure and thin-film composition by X-ray diffractometry and X-ray photoelectron spectroscopy. The film thickness was 120 nm, and the film composition was copper oxide.

Conditions:

Vaporizing chamber temperature: 50° C.; Reaction pressure: 100 Pa; Reaction time: 60 minutes; Substrate temperature: 150° C.; Carrier gas (Ar): 100 ml/min.; Oxidizing gas (oxygen): 200 ml/min.

Example 20

Production of Metallic-Copper Thin Film:

The copper compound (Compound No. 23) of the present invention obtained in Example 17 was used as a chemical vapor deposition material, and a metallic-copper thin film was produced on a silicon wafer substrate by thermal CVD according the following conditions by using the device illustrated in FIG. 3. The obtained thin film was subjected to film-thickness measurement by X-ray reflectometry and to a verification of thin-film structure and thin-film composition by X-ray diffractometry and X-ray photoelectron spectroscopy. The film thickness was 100 nm, and the film composition was metallic copper.

Conditions:

Material temperature: 50° C.; Reaction system pressure: 100 Pa; Reaction time: 60 minutes; Substrate temperature: 185° C.; Carrier gas (Ar): 100 ml/min.; Reactive gas: none.

Comparative Example 1

Production of Comparative Metallic-Copper Thin Film:

Comparative Compound 1 was used as a chemical vapor deposition material, and a metallic-copper thin film was produced on a silicon wafer substrate by thermal CVD according the following conditions by using the device illustrated in FIG. 3. The obtained thin film was subjected to film-thickness measurement by X-ray reflectometry and to a verification of thin-film structure and thin-film composition by X-ray diffractometry and X-ray photoelectron spectroscopy. The film thickness was 75 nm, and the film composition was metallic copper.

Conditions:

Vaporizing chamber temperature: 50° C.; Reaction pressure: 100 Pa; Reaction time: 60 minutes; Substrate temperature: 240° C.; Carrier gas (Ar): 100 ml/min.; Reactive gas: none.

Evaluation Example 3

The metallic-copper thin film obtained by Example 20 was compared with the comparative metallic-copper thin film obtained by Comparative Example 1. The results are shown in Table 3.

TABLE 3

| | Deposition rate of metallic-copper thin film (nm/h) | Average polycrystalline particle size of metallic-copper thin film (μm) | Electric resistance value (μΩ · cm) |
|---|---|---|---|
| Example 20 | 100 | 0.05 | 2 |
| Comparative Example 1 | 75 | 0.3 | 4.2 |

From Table 3, when Example 20 was compared with Comparative Example 1, it was found that: Example 20 had a higher metallic-copper thin-film deposition rate than Comparative Example 1; the average polycrystalline particle size of the metallic-copper thin film obtained by Example 20 was smaller than the average polycrystalline particle size of the comparative metallic-copper thin film obtained by Comparative Example 1; and the electric resistance value of the metallic-copper thin film obtained by Example 20 was more than twice lower than the electric resistance value of the comparative metallic-copper thin film obtained by Comparative Example 1. From the above, it was found that the present invention can provide a metallic-copper thin film having excellent characteristics.

The invention claimed is:

1. An alcohol compound of general formula (II):

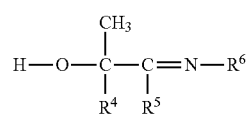

(II)

wherein, $R^4$ represents a methyl group or an ethyl group, $R^5$ represents a hydrogen atom, and $R^6$ represents a $C_{1-3}$ linear or branched alkyl group.

* * * * *